United States Patent
Kimmel

(10) Patent No.: US 10,210,951 B2
(45) Date of Patent: Feb. 19, 2019

(54) CROWDSOURCING INTRAORAL INFORMATION

(71) Applicant: Dustin Ryan Kimmel, San Francisco, CA (US)

(72) Inventor: Dustin Ryan Kimmel, San Francisco, CA (US)

( * ) Notice: Subject to any disclaimer, the term of this patent is extended or adjusted under 35 U.S.C. 154(b) by 372 days.

(21) Appl. No.: 14/817,072

(22) Filed: Aug. 3, 2015

(65) Prior Publication Data

US 2015/0339444 A1    Nov. 26, 2015

Related U.S. Application Data

(63) Continuation-in-part of application No. 13/831,940, filed on Mar. 15, 2013, now Pat. No. 9,117,363.

(60) Provisional application No. 61/612,398, filed on Mar. 19, 2012, provisional application No. 62/032,623, filed on Aug. 3, 2014, provisional application No. 62/163,975, filed on May 20, 2015.

(51) Int. Cl.
*G16H 10/65* (2018.01)
*H04L 29/08* (2006.01)
*G08C 17/02* (2006.01)
*A61F 4/00* (2006.01)

(52) U.S. Cl.
CPC ............ *G16H 10/65* (2018.01); *G08C 17/02* (2013.01); *H04L 67/32* (2013.01); *A61F 4/00* (2013.01); *G08C 2201/112* (2013.01); *G08C 2201/32* (2013.01)

(58) Field of Classification Search
CPC ........ G06F 19/323; G08C 17/02; H04L 67/32
USPC ....................................................... 709/213
See application file for complete search history.

(56) References Cited

U.S. PATENT DOCUMENTS

| | | | |
|---|---|---|---|
| 4,983,786 A | 1/1991 | Marzialo et al. | |
| 5,460,186 A | 10/1995 | Buchhold | |
| 5,523,745 A | 6/1996 | Fortune et al. | |
| 5,579,284 A | 11/1996 | May | |
| 5,603,065 A | 2/1997 | Baneth | |
| 5,631,669 A | 5/1997 | Stobbs et al. | |
| 5,792,067 A | 8/1998 | Karell | |
| 5,828,758 A | 10/1998 | Byce et al. | |
| 6,089,864 A * | 7/2000 | Buckner | A61F 5/56 433/6 |
| 6,222,524 B1 | 4/2001 | Salem et al. | |
| 6,400,353 B1 | 6/2002 | Ikehara et al. | |
| 7,071,844 B1 | 6/2006 | Moise | |
| 7,343,260 B1 * | 3/2008 | Kahn | G16H 10/60 702/122 |
| 8,734,341 B2 * | 5/2014 | Howell | A61B 5/4277 422/401 |
| 2003/0120183 A1 * | 6/2003 | Simmons | A61F 4/00 600/595 |

(Continued)

OTHER PUBLICATIONS

Nutt, Wolfgang et. al., Tongue-mouse for quadriplegics, J. Micromech. Microeng. 8, Aug. 12, 1997, p. 155-p. 157, IOP Publishing Ltd, UK.

*Primary Examiner* — Kevin T Bates
*Assistant Examiner* — Ronak Patel

(57) ABSTRACT

Techniques are described for detecting the presence or absence of certain molecules, analytes, or substances present in the oral cavity or characteristics of the saliva in the oral cavity. In particular, aspects of the invention disclose a systems, methods, apparatuses, and computer-readable media for detecting bio-markers.

17 Claims, 22 Drawing Sheets

(56) References Cited

U.S. PATENT DOCUMENTS

| | | | |
|---|---|---|---|
| 2005/0186540 A1* | 8/2005 | Taub | A61C 13/0004 |
| | | | 433/223 |
| 2006/0059364 A1* | 3/2006 | Fontijn | G07C 9/00563 |
| | | | 713/186 |
| 2007/0106138 A1 | 5/2007 | Beiski | |
| 2009/0092955 A1* | 4/2009 | Hwang | A46B 15/0002 |
| | | | 434/263 |
| 2009/0124917 A1* | 5/2009 | Hatlestad | A61B 5/0031 |
| | | | 600/529 |
| 2009/0309747 A1* | 12/2009 | Ghovanloo | A61F 4/00 |
| | | | 340/686.1 |
| 2010/0007512 A1* | 1/2010 | Ghovanloo | G06F 3/011 |
| | | | 340/4.11 |
| 2011/0141052 A1* | 6/2011 | Bernstein | G06F 3/016 |
| | | | 345/174 |
| 2011/0182918 A1* | 7/2011 | Kalnik | A61K 31/465 |
| | | | 424/175.1 |
| 2012/0166132 A1* | 6/2012 | Blom | G06Q 30/02 |
| | | | 702/127 |
| 2012/0319940 A1* | 12/2012 | Bress | G06F 3/017 |
| | | | 345/156 |
| 2013/0090931 A1* | 4/2013 | Ghovanloo | G06F 3/011 |
| | | | 704/275 |
| 2013/0137940 A1* | 5/2013 | Schafer | A61B 10/0012 |
| | | | 600/301 |
| 2013/0209954 A1* | 8/2013 | Prakash | A61B 1/0005 |
| | | | 433/29 |

* cited by examiner

CROWDSOURCING INTRAORAL INFORMATION

CROSS REFERENCE

The present application is a continuation-in-part application of (1) U.S. Non-Provisional application Ser. No. 13/831,940 filed Mar. 15, 2013, titled "Intraoral Communications and Processing Device," which further claims benefit of priority under 35 USC 119(e) of (2) U.S. Provisional Application No. 61/612,398, filed on Mar. 19, 2012, titled "Intraoral Processing and Wireless Communications Device," the content of which are incorporated herein by reference in its entirety.

The present application is also a non-provisional application of and claims the benefit and priority under 35 U.S.C. 119(e) of (3) U.S. Provisional Application No. 62/032,623, filed Aug. 3, 2014, titled "Intraoral Sensing Device and Method," and (3) U.S. Provisional Application No. 62/163,975, filed May 20, 2015, titled "Oral Sensing Device and Method." which are herein incorporated by reference in their entirety for all purposes.

TECHNICAL FIELD

Aspects of the disclosure relate to computing technologies. In particular, aspects of the disclosure relate to mobile computing device technologies, such as systems, methods, apparatuses, and computer-readable media for detecting certain markers. In particular, aspects of the invention disclose a systems, methods, apparatuses, and computer-readable media for detecting bio-markers.

BACKGROUND

Currently, several devices are available on the market that can detect certain activities (e.g., walking, running) and conditions (e.g., heart rate). Many of these devices are limited in the information that they can detect and provide, such as wristbands, with regard to a body. Devices that may provide a greater range or depth of information may be invasive (e.g., draw blood) and/or provide temporary data points of information.

BRIEF DESCRIPTION OF THE DRAWINGS

An understanding of the nature and advantages of various embodiments may be realized by reference to the following figures. In the appended figures, similar components or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION

Figure 1:
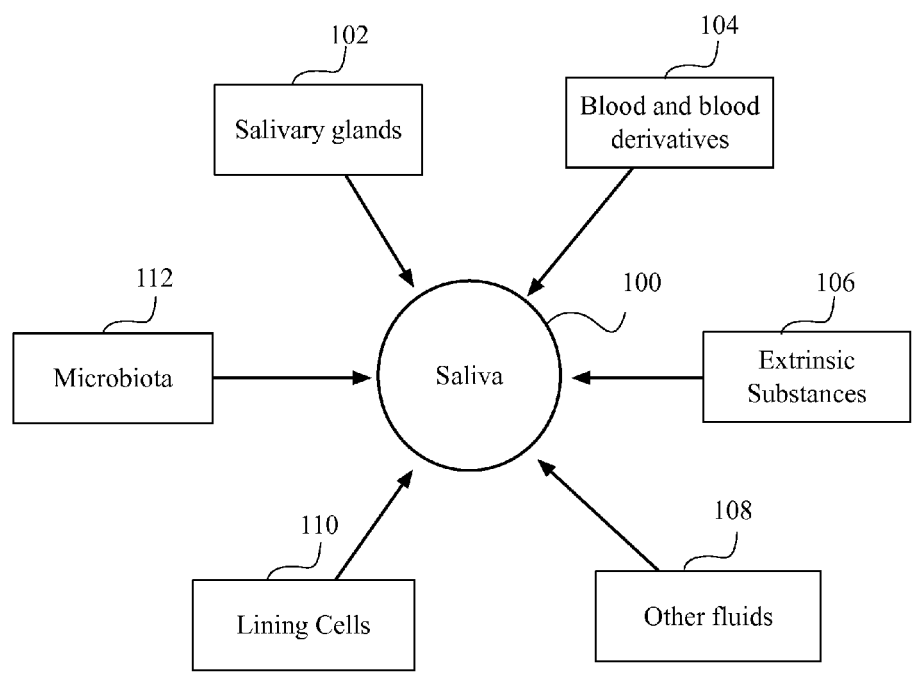
FIG. 1 illustrates example molecules and analytes that may be present in saliva.

The word "exemplary" is used herein to mean "serving as an example, instance, or illustration." Any embodiment or design described herein as "exemplary" is not necessarily to be construed as preferred or advantageous over other embodiments or designs.

Aspects of the disclosure relate to computing technologies. In particular, aspects of the disclosure relate to mobile computing device technologies, such as systems, methods, apparatuses, and computer-readable media for detecting certain markers. In particular, aspects of the invention disclose a systems, methods, apparatuses, and computer-readable media for detecting bio-markers.

In anatomy, the area known as "the mouth" is a nexus of biological processes, and can be capable of great sensation, dexterity, communication, and biological information. However, its harsh, dynamic and vulnerable environment makes sensing information, sending information, storing information, presenting a user interface to, and maintaining direct, prolonged access to the abilities and perspective of the mouth a difficulty.

In certain embodiments, according to embodiments described herein, a computing device is placed inside the oral cavity of a being (e.g., human being, animal) for detecting biomarkers. An embodiment of the present disclosure relates to an electronic device having an apparatus which includes a housing for use in a mouth environment of an animal and resistant to damage from bodily fluids and pressure. The housing can be placed in different locations of the oral cavity. The housing may include one or more of a power device, which can power the apparatus, a memory storage device, which can store and recall data; a communications subsystem, which communicates with one or more remote devices; an output device, which creates stimulus directly or indirectly observable in the mouth environment; an input device, which can create signals according to activity in the mouth environment and can send them to the memory storage device and/or processor; and a processor coupled to the memory storage device, the communication subsystem, the output device and the input device.

In certain embodiments, an apparatus, method, system and computer-readable medium is described for detecting various substances in the oral cavity. Various substances may include atoms, molecules, analytes, elements, certain mixtures and compounds. In certain embodiments, the various substances are suspended in saliva inside the oral cavity. In certain embodiments, an apparatus, method, system and computer readable medium is described for determining characteristics (e.g., viscosity, acidity, etc.) associated with the saliva in the oral cavity.

In one embodiment of the disclosure, components of the device may detect at least one or more molecules in an oral cavity using a self-contained device disposable in the oral cavity, and wirelessly sending information associated with the at least one molecule to an external device. In another embodiment, components of the device may detect at least one molecule in an oral cavity using a self-contained device disposable in the oral cavity, wherein the self-contained device comprises memory, and store information associated with the at least one molecule in the memory. In certain other embodiments, components of the device may detect at least one molecule in an oral cavity using a self-contained device disposable in the oral cavity, and perform an action in the oral cavity based on information associated with the at least one molecule.

In one aspect of the disclosure, components of the device detect molecules and/or analytes suspended in the saliva of the oral cavity. As shown in FIG. 1, components of a device may be configured to detect one or more types of molecules from the saliva 100 of the oral cavity. For example, components of the device may detect molecules originating from the salivary glands 102, such as water, proteins, electrolytes, and other small organic molecules, such as sugars, starch and carbohydrates.

Components of the device may also detect, in some instances, one or more of blood and blood derivatives 104, microbiota 112, lining cells 110, extrinsic substances 106, and other fluids 108. Blood and blood derivatives 104 may include intraoral bleeding (serum and cells), gingival crevicular fluid (GCF: serum exudate and inflammatory cells). Microbiota 112 may include oral bacteria (enzymes and bacterial products), viruses and fungi. Lining cells 110 may include epithelial keratins. Extrinsic substances 106 may include food particles, toothpaste, mouth rinse, air impurities, such as smoke particles dissolved or suspended in saliva.

Other molecules or group of molecules, such as cortisol, insulin, and other hormonal molecules may be detected in the saliva. Cortisol may be produced in the adrenal cortex. Unbound or free cortisol (i.e., cortisol that is not bound to proteins) is active and due to its low molecular weight and nature, enters cells by passive diffusion which makes it feasible to measure the free cortisol in the saliva. In certain instances, the detection of Cortisol in the oral cavity beyond various thresholds may indicate varying levels of stress that the being may be undergoing.

Insulin is a peptide hormone, produced in the pancreas and is essential for regulating carbohydrate and fat metabolism in the body. In a normal functioning body, insulin is provided in a constant proportion in the body. However, people or animals suffering from diabetics, in some instance, either do not produce enough insulin or their bodies become resistant to insulin and may need higher doses of insulin than what is produced by their body. Traces of insulin are also detectable in the saliva that is proportional to the insulin present in the blood serum. In certain embodiments, as described herein, components of the computing device may also detect insulin in the saliva.

Other molecules and substances suspended in the saliva, such as sugar, carbohydrates and starch may also be detected by components of the device. Generally, in certain embodiments, components of the device may also be configured to estimate or determine or enable estimation and determination of the number of calories consumed by the being with the device disposed in their oral cavity over a period of time.

The housing can be implemented using a variety of known and novel techniques without deviating from the scope of the invention. A few non-limiting examples for implementing the housing are described in FIG. 16-FIG. 21. The retainer and/or bridge may allow the user to wield the device from the lower jaw with the tongue in a relaxed, forward position. A maxilla retainer (or upper palate retainer) and/or bridge may provide the user with a large surface area for performing tactile functions by the tongue by touching the sensor placed against the upper palate. The dental implant housing is also advantageous because it allows stimulation of deeper gum tissue. Other considerations for the placement of the device in the oral cavity may also include the level of exposure to saliva to certain sensors coupled to the housing.

The electronic device further includes a power device deriving power from one or more of energy of an internal battery, wireless energy transfer, energy from chemical or electrical reactions with the surrounding mouth environment, energy from chemical reactions with the blood, saliva or other excretions of the user, energy from the physical flow of the bloodstream of the user, and kinetic energy of the motion of the animal.

The electronic device can further include a communications device that can be one or more of an EMF transmitter/receiver device, a Radio Frequency Identification (RFID) tag, a Bluetooth device, a WiFi device, infrared device, and a cellular device.

The electronic device can further include an output device that can be one or more of a mechanical wave generator device, an electrical stimulator device, a vibration device, and a physical release device.

The electronic device can further include an input device that can be one or more of a touch sensor device, a material sensor device, a pressure sensor device, a movement tracking sensor device, an orientation sensor device, an acceleration sensor device, a temperature sensor device, an air sensor device, and a light sensor device.

In one implementation, the electronic device may include a plurality of electrodes for determining various characteristics of the saliva in the oral cavity. For example, such characteristics may include the electrical properties, such as rate of flow of electrons through the saliva in the oral cavity. The electrodes may be coupled to various portions of the housing described in example implementations of FIG. 16-FIG. 21.

The electronic device can further include a memory storage device that can include one or more application programs. The storage may be volatile memory or non-volatile memory.

Another embodiment of the present disclosure relates to an electronic device having an apparatus including a housing inside the mouth of a being and resistant to damage from bodily fluids and pressure. The housing can be one of a tongue piercing, a lip piercing, and a cheek piercing. The housing can further include: a power device for powering the apparatus; a processor communicatively coupled to an output device, input device, memory storage device, and communications subsystem. The output device can generate one or more stimuli in the mouth environment. The input device can create signals associated with the analog input in the mouth. The memory storage device can be communicatively coupled to the processor for storing and recalling data. The communications subsystem can communicate with one or more remote devices. The housing can include a piercing jewelry of barbell shape. The barbell shape is advantageous because it allows the housing to stay in the tongue but still to rotate in its piercing site.

The electronic device can further include a power device which can derive power from the energy of an internal battery.

The electronic device can further include a communications device which can include an EMF transmitter/receiver device.

The electronic device can further include an output device includes one or more of a mechanical wave generator device, an electrical stimulator device, a vibration device, and a physical release device.

The electronic device can further include an input device which can include one or more of a touch sensor device, a pressure sensor device, a movement tracking sensor device, an orientation sensor device, an acceleration sensor device, a temperature sensor device, an air sensor device, and a light sensor device.

The electronic device can further include a memory storage device that can include one or more application programs.

An exemplary method for communicating includes generating a stimulus to a tongue of a user to communicate a user interface to the user; detecting an analog input from an environment of the tongue of the user; and interpreting the analog input from the environment as one or more user commands.

In certain embodiments the stimulus can be generated using a tongue-pierced device. In certain embodiments the stimulus can be generated using a device anchored to a tooth or a teeth of the mandible. In certain embodiments the stimulus can be generated using a device anchored to a tooth or a teeth of the upper jaw. In certain embodiments the stimulus can be generated using a device implanted in (or attached to an implant in) the maxilla or mandible. In certain embodiments the stimulus can be generated by one or more of creating vibration, causing electric shocks from electrodes, and dispensing matter. In certain embodiments the analog input can be detected from one or more of sensing touch, orientation, acceleration, pressure, and sound at the environment of the tongue.

In an example non-transitory computer readable storage medium, wherein the non-transitory computer readable storage medium comprises instructions executable by a processor, the instructions comprising instructions to generate a stimulus to a tongue of a user to communicate a user interface to the user; detect an analog input from an environment of the tongue of the user, and interpret the analog input from the environment as one or more user commands.

In one implementation of the non-transitory computer readable storage medium the stimulus can be generated using a tongue-pierced device. In another implementation of the non-transitory computer readable storage medium the stimulus can be generated using a device anchored to a tooth or a teeth of the mandible and/or maxilla. In another implementation of the non-transitory computer readable storage medium the stimulus can be generated using a device implanted in (or attached to an implant in) the maxilla or mandible. In another implementation of the non-transitory computer readable storage medium the stimulus can be generated by one or more of creating vibration, causing electric shocks from electrodes, and dispensing matter.

In another implementation of the non-transitory computer readable storage medium the analog input can be detected from one or more of sensing touch, orientation, acceleration, pressure, and sound at the environment of the tongue.

An example device or apparatus for communicating includes means for generating a stimulus to a tongue of a user to communicate a user interface to the user, means for detecting an analog input from an environment of the tongue of the user, and means for interpreting the analog input from the environment as one or more user commands.

In certain embodiments the device or apparatus can include means for generating the stimulus using a tongue-pierced device. In certain embodiments the device or apparatus can include means for generating the stimulus using a device anchored to a tooth or a teeth of the mandible or maxilla. In certain embodiments the device or apparatus can include means for generating the stimulus using a device implanted in (or attached to an implant in) the maxilla or mandible. In certain embodiments the device or apparatus can include means for generating the stimulus by causing vibration, causing electric shocks from electrodes, and dispensing matter.

In certain embodiments the device or apparatus can include means for detecting the analog input from one or more of sensing touch, orientation, acceleration, pressure, and sound at the environment of the tongue.

In addition to the sensor described above, the device may include molecule sensors for detecting certain molecules present in the saliva. Certain embodiments of such molecule sensors are presented in FIG. 6 and FIG. 7.

Figure 2:
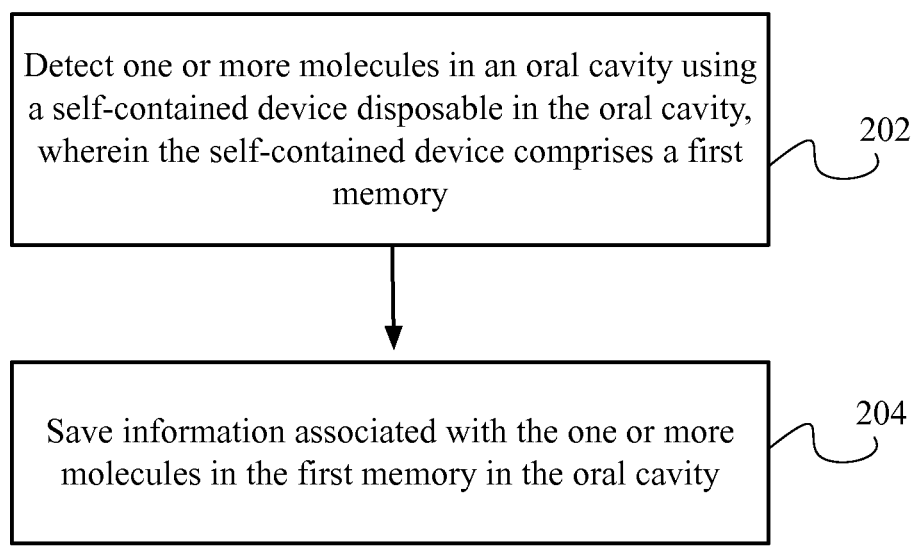
FIG. 2 is an example flow diagram illustrating detecting a molecule in the oral cavity according to one example embodiment of the disclosure.

FIG. 2 is an example flow diagram illustrating detecting a molecule in the oral cavity according to one example embodiment of the disclosure. As described herein, a being may refer to a human being or an animal. The steps performed in reference to FIG. 2 may be performed using a processor, hardware or analog and/or digital logic, analog and/or digital sensor logic, or any combination thereof. In certain implementations, certain components described in reference to FIG. 22 may be used in performing steps/blocks described in FIG. 2.

At step 202, components of the device, detect one or more molecules in an oral cavity using a self-contained device disposable in the oral cavity, wherein the self-contained device comprises a first memory. Several different modes or techniques may be used for detecting one or more molecules in an oral cavity. In certain embodiments, the one or more molecules are suspended in the saliva and detected from the saliva.

In one implementation, a plasmonic interferometer sensor may be used for detecting an at least one molecule in the oral cavity. More example details regarding the functioning of a plasmonic interferometer are described in FIG. 6. In certain implementations, a molecularly imprinted polymer sensor is used for detecting an at least one molecule in the oral cavity. More example details regarding the functioning of a molecularly imprinted polymer are described in FIG. 7. In yet another example implementation, a change in the conductivity of saliva in the oral cavity may be used for detecting an at least one molecule in the oral cavity.

In certain implementations, detecting an at least one molecule in the oral cavity comprises detecting a biological indicator for a being. For example, detecting certain molecules in the oral cavity may provide an indication of an early onset of an ailment or the severity of the ailment. For example, detecting the level of glucose may indicate the severity of a diabetic attack or the need for insulin or other medication to control the glucose level.

Furthermore, detecting an at least one molecule in the oral cavity may provide an indication of the type of food, liquid, caloric intake, sugar intake, or other specific molecules, ingredients or mixers swallowed or ingested by a being, either immediately or over a prolonged period of time.

Moreover, detecting an at least one molecule in the oral cavity may provide a stress marker associated with the being. For example, components of the device may detect cortisol molecules that may provide an indication of the level of stress experienced by the being at any given point in time or over a period of time.

In certain implementations, the data received by the device is extrapolated to provide an accurate indicator. For example, the glucose level in the saliva may be $1/100^{th}$ of what is present in the blood and generally measuring the glucose in the saliva at any given time may not be an accurate level of glucose in the blood stream, at least in certain implementations. Instead, the device may be capable of detecting the glucose in the oral cavity for several hundreds or even thousands of detecting iterations, perform data analysis on a much wider dataset, filter out noise from the data and presenting a much more acceptable range of accuracy for the provided indicator.

The self-contained device may be positioned in one or more locations in the oral cavity. Example locations for the placement of the self-contained device may include, but are not limited to the lower jaw, upper jaw, tooth retainer, tooth, or tongue piercing. Some examples of such placements are described in further detail in FIGS. 16-21.

At step 204, components of the device, may save information associated with the one or more molecules in the first memory in the oral cavity. The information may be stored temporarily by the device for further processing, as described in further detail in FIGS. 3, 4 and 5.

It should be appreciated that the specific steps illustrated in FIG. 2 provide a particular method of switching between modes of operation, according to an embodiment of the present invention. Other sequences of steps may also be performed accordingly in alternative embodiments. For example, alternative embodiments of the present invention may perform the steps/blocks outlined above in a different order. To illustrate, a user may choose to change from the third mode of operation to the first mode of operation, the fourth mode to the second mode, or any combination therebetween. Moreover, the individual steps/blocks illustrated in FIG. 2 may include multiple sub-steps that may be performed in various sequences as appropriate to the individual step. Furthermore, additional steps/blocks may be added or removed depending on the particular applications. One of ordinary skill in the art would recognize and appreciate many variations, modifications, and alternatives of the process.

Figure 3:
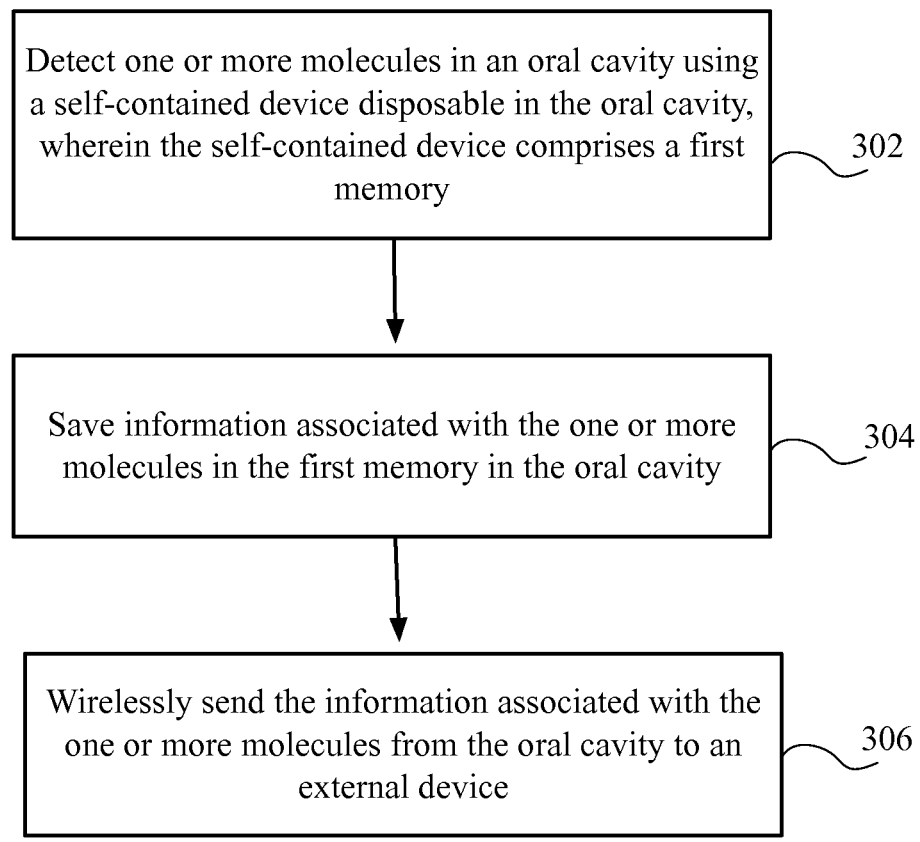
FIG. 3 is an example flow diagram illustrating detecting a molecule in the oral cavity according to one example embodiment of the disclosure.

FIG. 3 is an example flow diagram illustrating detecting a molecule in the oral cavity according to one example embodiment of the disclosure. As described herein, a being may refer to a human being or an animal. The steps performed in reference to FIG. 3 may be performed using a processor, hardware or analog and/or digital logic, analog and/or digital sensor logic, or any combination thereof. In certain implementations, certain components described in reference to FIG. 22 may be used in performing steps/blocks described in FIG. 3.

Step 302 of FIG. 3 is similar to step 202 of FIG. 2, wherein, components of the device, detect one or more molecules in an oral cavity using a self-contained device disposable in the oral cavity, wherein the self-contained device comprises a first memory.

Similarly, step 304 of FIG. 3 is similar to step 204 of FIG. 2, wherein components of the device save information associated with the one or more molecules in the first memory in the oral cavity.

At step 306, component of the device, may further wirelessly send information associated with the one or more molecules from the oral cavity to an external device. In one instance, the device may send information directly or through intermediate devices to a crowdsourcing server, such as the server described in FIG. 14. The crowdsourcing server may aggregate date from multiple devices. In certain implementations, such data is anonymized at the device and/or the server. The data may be used in determining certain patterns associated with bio-indicators. For example, links between detection of certain molecules and certain ailments may be studied using the aggregated data from the plurality of devices.

In another embodiment, the information may be sent to an emergency service for reacting to detection of an emergency situation, such as an asthma attack, diabetic attack or any other ailment that may need immediate attention.

In yet another embodiment, the information may be sent to a backend server, where the data may be stored for later retrieval or analysis by the user or a third-party trusted entity for further processing and analysis. For example, the data may be stored by a hospital for the being.

It should be appreciated that the specific steps illustrated in FIG. 3 provide a particular method of switching between modes of operation, according to an embodiment of the present invention. Other sequences of steps may also be performed accordingly in alternative embodiments. For example, alternative embodiments of the present invention may perform the steps/blocks outlined above in a different order. To illustrate, a user may choose to change from the third mode of operation to the first mode of operation, the fourth mode to the second mode, or any combination therebetween. Moreover, the individual steps/blocks illustrated in FIG. 3 may include multiple sub-steps that may be performed in various sequences as appropriate to the individual step. Furthermore, additional steps/blocks may be added or removed depending on the particular applications. One of ordinary skill in the art would recognize and appreciate many variations, modifications, and alternatives of the process.

Figure 4:
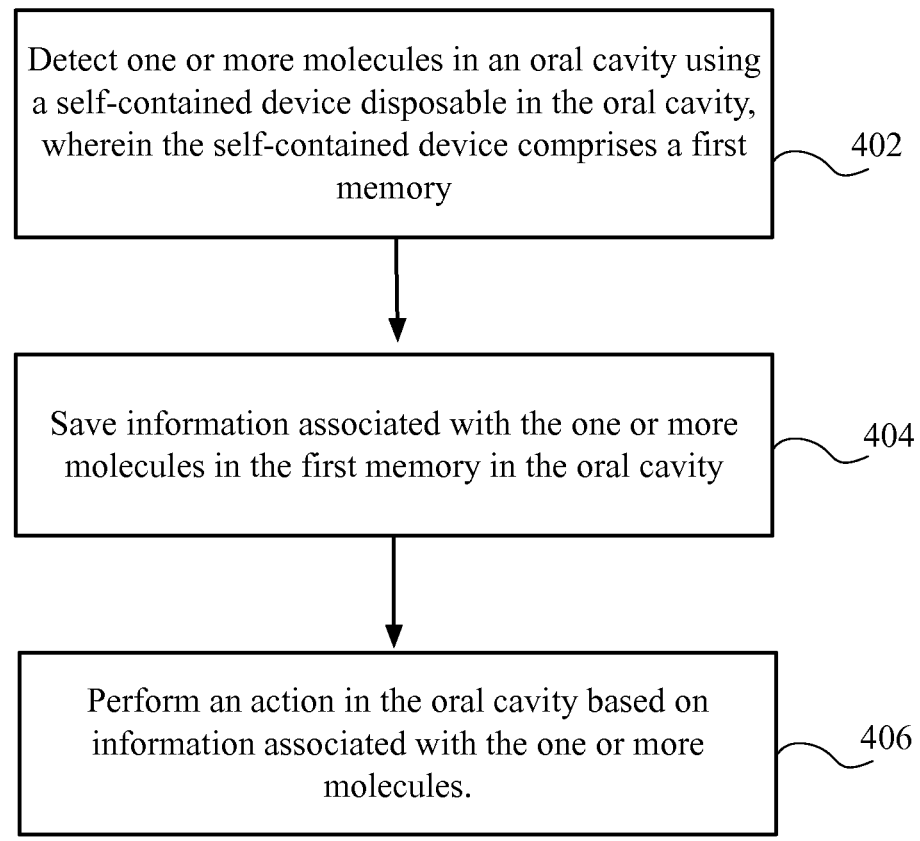
FIG. 4 is an example flow diagram illustrating detecting a molecule in the oral cavity according to one example embodiment of the disclosure.

FIG. 4 is an example flow diagram illustrating detecting a molecule in the oral cavity according to one example embodiment of the disclosure. As described herein, a being may refer to a human being or an animal. The steps performed in reference to FIG. 4 may be performed using a processor, hardware or analog and/or digital logic, analog and/or digital sensor logic, or any combination thereof. In certain implementations, certain components described in reference to FIG. 22 may be used in performing steps/blocks described in FIG. 4.

Step 402 of FIG. 4 is similar to step 202 of FIG. 2, wherein, components of the device, detect one or more molecules in an oral cavity using a self-contained device disposable in the oral cavity, wherein the self-contained device comprises a first memory.

Similarly, step 404 of FIG. 4 is similar to step 204 of FIG. 2, wherein components of the device save information associated with the one or more molecules in the first memory in the oral cavity.

At step 406, components of the device, may further perform an action in the oral cavity based on information associated with the one or more molecules. For example, the device may release a small dose of medication for a condition detected based on detecting one or more molecules in the oral cavity. For instance, in response to detecting an indication of a heart attack, the device may be configured to release a small dose of Asprin®, NSAID or any other medication to prevent further deterioration of the beings condition. Similarly, the device may release a small dose of insulin, in response to detecting a spike in glucose or take similar remedial steps in response to detecting an asthma attack.

In certain implementations, the device may also be configured to provide other feedback to the user, such as provide a low voltage and current shock or provide a vibration. For example, the device may provide feedback to the user in response to detecting a stress marker, such as cortisol in the saliva beyond a certain threshold. In some instances, the feedback may remind the user to relax or avoid the stressful activity. The device may be further configured to continually provide feedback to the user, as long as the user continues to engage in the stressful activity to discourage such activities.

It should be appreciated that the specific steps illustrated in FIG. 4 provide a particular method of switching between modes of operation, according to an embodiment of the present invention. Other sequences of steps may also be performed accordingly in alternative embodiments. For example, alternative embodiments of the present invention may perform the steps/blocks outlined above in a different order. To illustrate, a user may choose to change from the third mode of operation to the first mode of operation, the fourth mode to the second mode, or any combination therebetween. Moreover, the individual steps/blocks illustrated in FIG. 4 may include multiple sub-steps that may be performed in various sequences as appropriate to the individual step. Furthermore, additional steps/blocks may be added or removed depending on the particular applications. One of ordinary skill in the art would recognize and appreciate many variations, modifications, and alternatives of the process.

Figure 5:
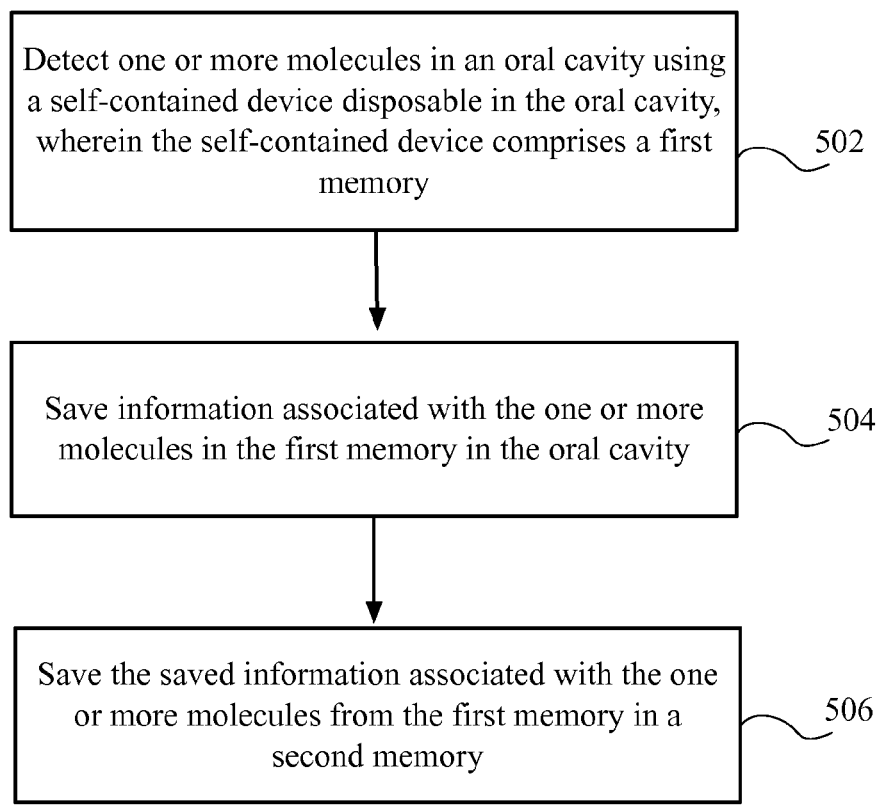
FIG. 5 is an example flow diagram illustrating detecting a molecule in the oral cavity according to one example embodiment of the disclosure.

FIG. 5 is an example flow diagram illustrating detecting a molecule in the oral cavity according to one example embodiment of the disclosure. As described herein, a being may refer to a human being or an animal. The steps performed in reference to FIG. 5 may be performed using a processor, hardware or analog and/or digital logic, analog and/or digital sensor logic, or any combination thereof. In certain implementations, certain components described in reference to FIG. 22 may be used in performing steps/blocks described in FIG. 5.

Step 502 of FIG. 5 is similar to step 202 of FIG. 2, wherein, components of the device, detect one or more molecules in an oral cavity using a self-contained device disposable in the oral cavity, wherein the self-contained device comprises a first memory.

Similarly, step 504 of FIG. 5 is similar to step 204 of FIG. 2, wherein components of the device save information associated with the one or more molecules in the first memory in the oral cavity.

At step 506, component of the device, may comprise saving the saved information associated with the one or more molecules from the first memory to a second memory.

In some implementations, the first memory may be a volatile memory and the second memory may be non-volatile memory. The first memory may be used as a temporary store before the data is further processed and/or stored in the second memory for longer periods of storage.

In certain embodiments, the information associated with the one or more molecules is stored for further processing and actions at a later point in time. For example, the information associated with the molecules detected may be monitored for a period of time. If certain number of molecules are detected (or not detected in certain implementations) then components of the device may take additional steps such as wirelessly communicating with an external device (FIG. 3) or taking an action (FIG. 4).

In certain embodiments, the information may be logged for retrieval by another system at a later point in time for further analysis. For example, the device may store detection of certain molecules determined to fit a certain criteria (e.g., type, time of the day, frequency, etc.) with a timestamp for later retrieval and analysis.

It should be appreciated that the specific steps illustrated in FIG. 5 provide a particular method of switching between modes of operation, according to an embodiment of the present invention. Other sequences of steps may also be performed accordingly in alternative embodiments. For example, alternative embodiments of the present invention may perform the steps/blocks outlined above in a different order. To illustrate, a user may choose to change from the third mode of operation to the first mode of operation, the fourth mode to the second mode, or any combination therebetween. Moreover, the individual steps/blocks illustrated in FIG. 5 may include multiple sub-steps that may be performed in various sequences as appropriate to the individual step. Furthermore, additional steps/blocks may be added or removed depending on the particular applications. One of ordinary skill in the art would recognize and appreciate many variations, modifications, and alternatives of the process.

Figure 6:
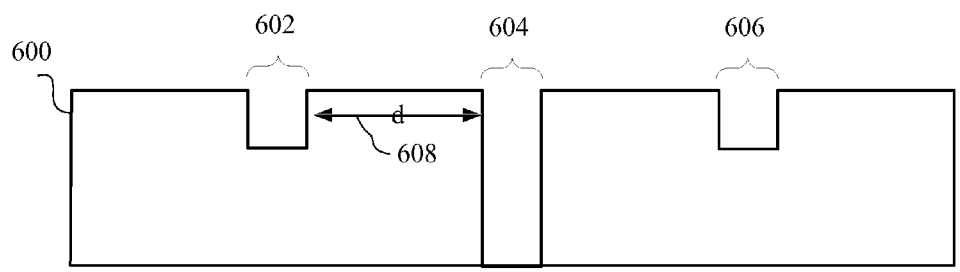
FIG. 6 is an illustration of an example of a portion of a biomolecule sensor for detecting a molecule in the saliva according to one embodiment of the disclosure.

FIG. 6 is an illustration of an example of a portion of a biomolecule sensor for detecting a molecule in the saliva according to one embodiment of the disclosure. In one implementation, a biosensor chip that uses plasmonic interferometers could be used for detecting various substances in the saliva. For example, such a chip when coupled to the device disposable in the oral cavity can detect substances, such as glucose levels. This may be preferable over drawing blood, that may be painful and provide the user with only a one-time indicator of their health, instead of a periodic measurement of important indicators from the saliva, as described according to embodiments of the disclosure.

Such techniques take advantage of nanotechnology and surface plasmonics, which uses the interaction between electrons associated with molecules and photons to detect various substances. For example, researchers at Brown university have manufactured a sensor that has thousands of plasmonic interferometers onto a fingernail-size biochip and measured the concentration of glucose molecules in water on the chip. Their result confirms that the specially designed biochip could detect glucose levels similar to the levels found in human saliva. Glucose in human saliva is typically about 100 times less concentrated than in the blood.

As illustrated in FIG. 6, a slit 604 is carved out in the sensor with two grooves (602, 606) on either side of the slit 604. The slit 604 captures incoming photons and confines them. The grooves (602, 606), meanwhile, scatter the incoming photons, which interact with the free electrons bounding around on the sensor's metal surface. Those free electron-photon interactions create a surface plasmon polariton, a special wave with a wavelength that is narrower than a photon in free space. These surface plasmon waves move along the sensor's surface until they encounter the photons in the slit, much like two ocean waves coming from different directions and colliding with each other. This "interference" between the two waves determines maxima and minima in the light intensity transmitted through the slit 604. The presence of an analyte (the chemical being measured) on the sensor surface generates a change in the relative phase difference between the two surface plasmon waves, which in turns causes a change in light intensity, measured in real time. Essentially, the slit 604 acts as a mixer for the three beams—the incident light and the surface plasmon waves. The phase shift for an interferometer may be adjusted by changing the distance (d) 608 between the grooves (602, 606) and the slit 604, to detect multiple analytes.

Figure 7:
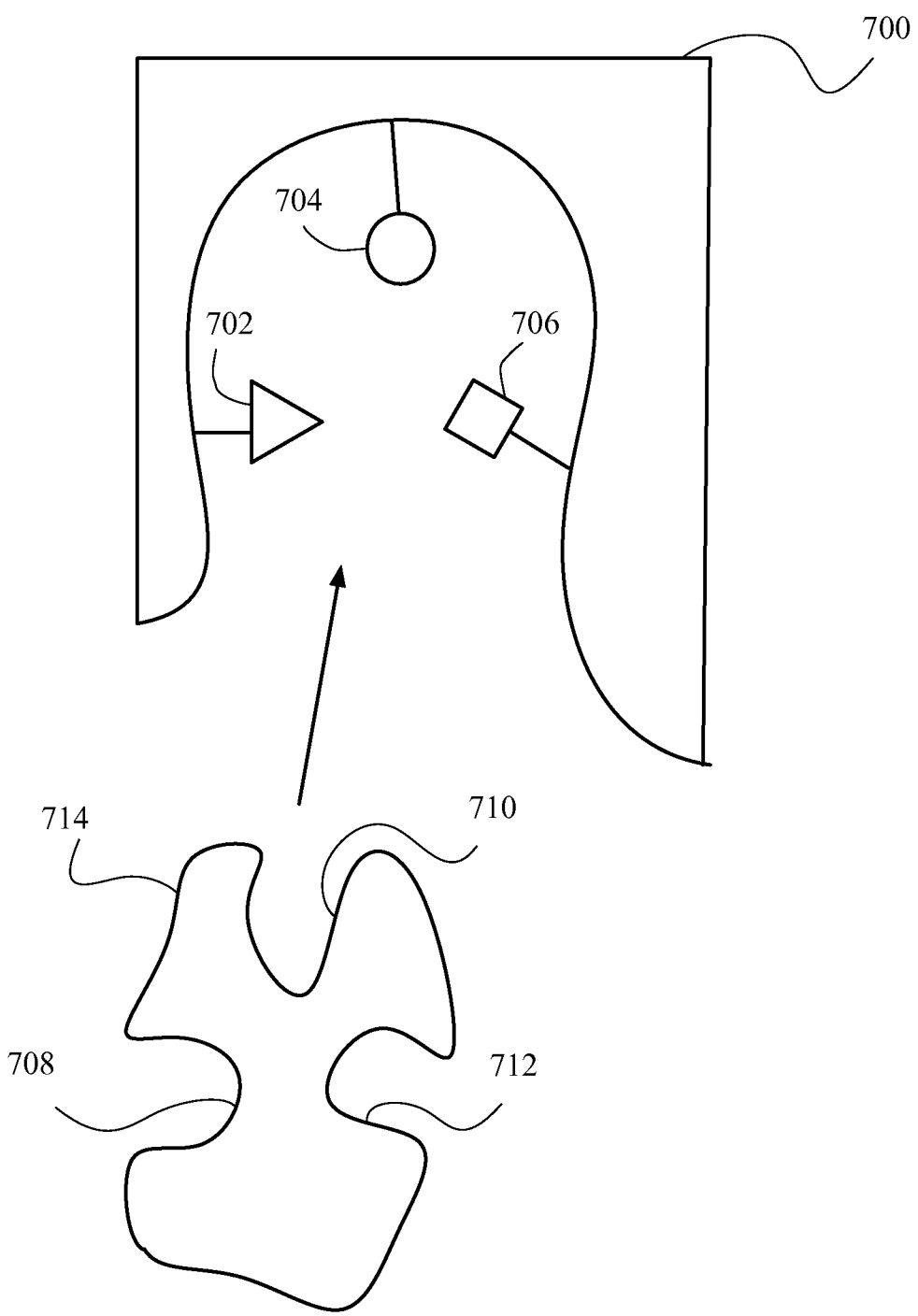
FIG. 7 is an illustration of another example portion of a biomolecule sensor for detecting a molecule in the saliva according to one embodiment of the disclosure.

FIG. 7 is an illustration of another example portion of a biomolecule sensor for detecting a molecule in the saliva according to one embodiment of the disclosure. In one embodiment, a molecular imprinted polymer (MIP) sensor may be used for detecting various molecules and/or analytes in the saliva.

An MIP sensor is a polymer that has been processed using the molecular imprinting technique which leaves cavities in polymer matrix with affinity to a selected molecule. The process usually involves initiating the polymerization of monomers in the presence of a template molecule that is extracted afterwards, thus leaving a complementary cavity behind. The target molecule fits in these cavities resulting in a match and detection of the target molecule.

Molecular imprinting is, in fact, making an artificial tiny lock for a specific molecule that serve as a miniature key. The MIP sensor material is etched to create specific cavities which in size, shape and functional groups, fit the target molecule.

FIG. 7 illustrates an example of such a cavity 700 for detecting a target molecule 714. The cavity may have irregularities (702, 704 and 706) specific to the target molecules. For example, irregularity 702 of the cavity 700 may correspond to groove 708 of the target molecule 714.

Similarly, irregularities 704 and 706 may correspond to grooves 710 and 712 of the target molecule 714, respectively.

Techniques described in FIG. 6 and FIG. 7 for detecting different analytes and molecules associated with the analytes are only examples of detection techniques and are not meant to limit embodiments of the inventions. Other known techniques for detecting electrons, molecules, analytes, and/or chemical substances by persons skilled in the art may be used without deviating from the scope of the invention.

Figure 8:
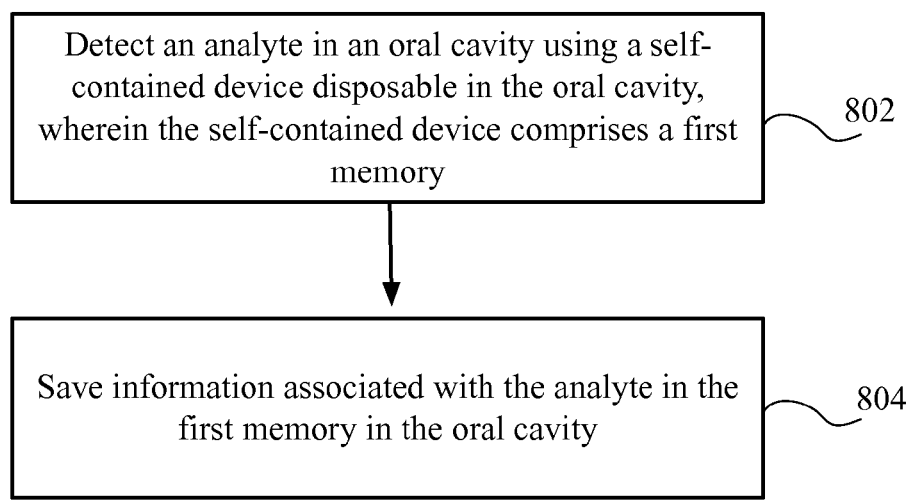
FIG. 8 is an example flow diagram illustrating detecting an analyte in the oral cavity according to one example embodiment of the disclosure.

FIG. 8 is an example flow diagram illustrating detecting an analyte in the oral cavity according to one example embodiment of the disclosure. As described herein, a being may refer to a human being or an animal. The steps performed in reference to FIG. 8 may be performed using a processor, hardware or analog and/or digital logic, analog and/or digital sensor logic, or any combination thereof. In certain implementations, certain components described in reference to FIG. 22 may be used in performing steps/blocks described in FIG. 8.

Step 802, components of the device detect an analyte in an oral cavity using a self-contained device disposable in the oral cavity, wherein the self-contained device comprises a first memory. In certain instances, analyte may refer to a substance or chemical constituent that may be of interest in an analytical procedure. In certain embodiments, the analyte may be suspended in saliva in the oral cavity.

In step 804, components of the device, save information associated with the analyte in the first memory in the oral cavity. In certain implementations, the first memory may be volatile memory and used as temporary storage for further processing the information associated with the analyte. For example, in some implementations, the information associated with the analyte may be wirelessly sent to a second device, as described in FIG. 3. In certain implementations, further analysis of the stored data may result in taking certain actions by the device within the oral cavity, as described in FIG. 4. In certain other implementations, the information associated may be stored in a second memory for further processing at a later point in time, as described in FIG. 5. The second memory may be a non-volatile memory.

It should be appreciated that the specific steps illustrated in FIG. 8 provide a particular method of switching between modes of operation, according to an embodiment of the present invention. Other sequences of steps may also be performed accordingly in alternative embodiments. For example, alternative embodiments of the present invention may perform the steps/blocks outlined above in a different order. To illustrate, a user may choose to change from the third mode of operation to the first mode of operation, the fourth mode to the second mode, or any combination therebetween. Moreover, the individual steps/blocks illustrated in FIG. 8 may include multiple sub-steps that may be performed in various sequences as appropriate to the individual step. Furthermore, additional steps/blocks may be added or removed depending on the particular applications. One of ordinary skill in the art would recognize and appreciate many variations, modifications, and alternatives of the process.

Figure 9:
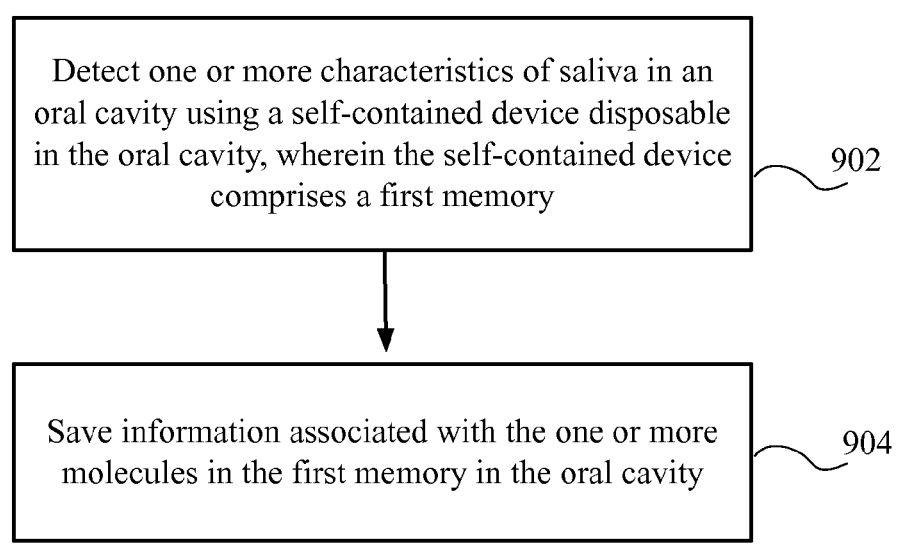
FIG. 9 is an example flow diagram illustrating detecting one or more characteristics of saliva in the oral cavity according to one example embodiment of the disclosure.

FIG. 9 is an example flow diagram illustrating detecting one or more characteristics of saliva in the oral cavity according to one example embodiment of the disclosure. As described herein, a being may refer to a human being or an animal. The steps performed in reference to FIG. 9 may be performed using a processor, hardware or analog and/or digital logic, analog and/or digital sensor logic, or any combination thereof. In certain implementations, certain components described in reference to FIG. 22 may be used in performing steps/blocks described in FIG. 9.

At step 902, components of the device, detect one or more characteristics in an oral cavity using a self-contained device disposable in the oral cavity, wherein the self-contained device comprises a first memory. Several different modes or techniques may be used for detecting one or more characteristics of the saliva in an oral cavity.

In certain implementation, a change in the conductivity of saliva in the oral cavity may be used for detecting characteristics associated with the saliva in the oral cavity. In other implementations, the acidity may be used in determining the characteristics of the saliva. Examples of characteristics of the saliva include, but are not limited to moisture, viscosity, pH, salinity, acidity, and conductivity of the saliva.

In certain implementations, detecting an at least one characteristic of the saliva in the oral cavity comprises detecting a biological indicator or biomarker for a being. For example, detecting certain characteristics in the oral cavity may provide an indication of several conditions, such as an early onset of an ailment or the severity of the ailment, thirst, hunger, or stress.

In certain implementations, the data received by the device is extrapolated to provide an accurate indicator. In some instances, in the oral cavity several hundreds or even thousands of detecting iterations are used to perform data analysis on a wide dataset and filter out noise from the data and present an acceptable range of accuracy for the provided indicator.

The self-contained device may be positioned in one or more locations in the oral cavity. Example locations for the placement of the self-contained device may include, but are not limited to the lower jaw, upper jaw, tooth retainer, tooth, or tongue piercing. Some examples of such placements are described in further detail in FIGS. 16-21.

At step 904, components of the device, may save information associated with the one or more characteristics in the first memory in the oral cavity. The information may be stored temporarily by the device for further processing, as described in further detail in FIGS. 10, 11 and 12.

It should be appreciated that the specific steps illustrated in FIG. 9 provide a particular method of switching between modes of operation, according to an embodiment of the present invention. Other sequences of steps may also be performed accordingly in alternative embodiments. For example, alternative embodiments of the present invention may perform the steps/blocks outlined above in a different order. To illustrate, a user may choose to change from the third mode of operation to the first mode of operation, the fourth mode to the second mode, or any combination therebetween. Moreover, the individual steps/blocks illustrated in FIG. 9 may include multiple sub-steps that may be performed in various sequences as appropriate to the individual step. Furthermore, additional steps/blocks may be added or removed depending on the particular applications. One of ordinary skill in the art would recognize and appreciate many variations, modifications, and alternatives of the process.

Figure 10:
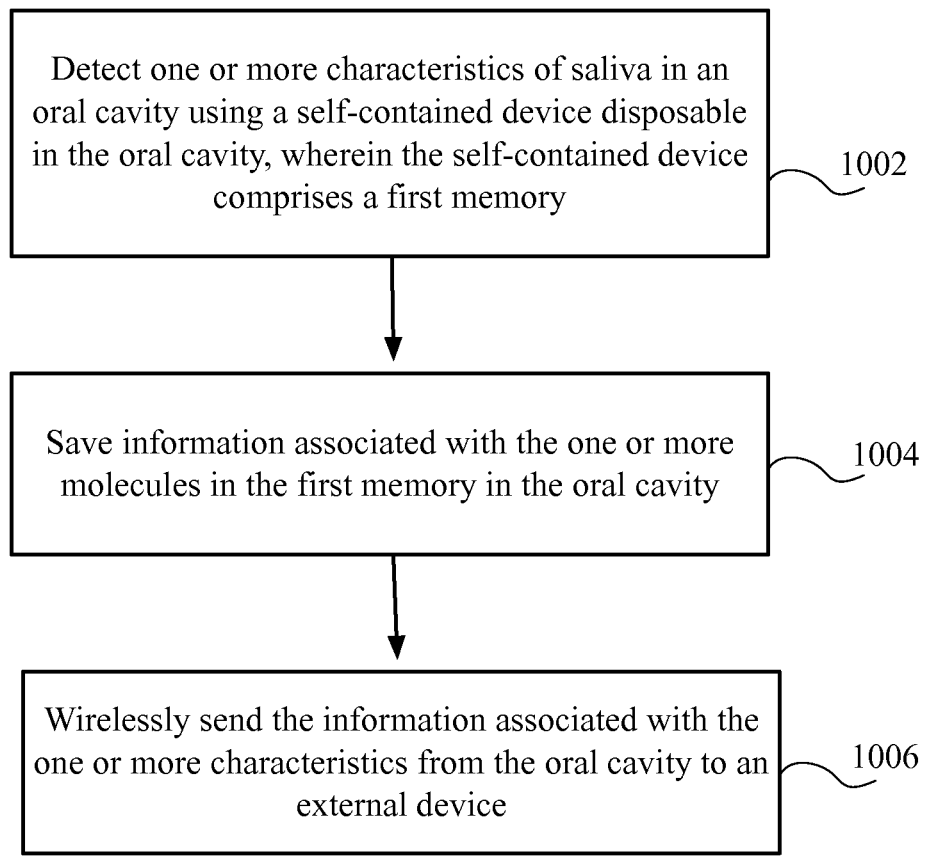
FIG. 10 is an example flow diagram illustrating detecting one or more characteristics associated with saliva in the oral cavity according to one example embodiment of the disclosure.

FIG. 10 is an example flow diagram illustrating detecting one or more characteristics associated with saliva in the oral cavity according to one example embodiment of the disclosure. As described herein, a being may refer to a human being or an animal. The steps performed in reference to FIG. 10 may be performed using a processor, hardware or analog and/or digital logic, analog and/or digital sensor logic, or any combination thereof. In certain implementations, certain components described in reference to FIG. 22 may be used in performing steps/blocks described in FIG. 10.

Step 1002 of FIG. 10 is similar to step 902 of FIG. 9, wherein, components of the device, detect one or more characteristics of the saliva in an oral cavity using a self-contained device disposable in the oral cavity, wherein the self-contained device comprises a first memory.

Similarly, step 1004 of FIG. 10 is similar to step 904 of FIG. 9, wherein components of the device save information associated with the one or more characteristics in the first memory in the oral cavity.

At step 1006, component of the device, may further wirelessly send information associated with the one or more characteristics from the oral cavity to an external device. In one instance, the device may send information directly or through intermediate devices to a crowdsourcing server, such as the server described in FIG. 14. The crowdsourcing server may aggregate date from multiple devices. In certain implementations, such data is anonymized at the device and/or the server. The data may be used in determining certain patterns associated with bio-indicators. For example, links between detection of certain characteristics of the saliva and certain conditions (thirst, hunger, stress, etc.) may be determined using the aggregated data from the plurality of devices.

In another embodiment, the information may be sent to an emergency service for reacting to detection of an emergency situation, such as an asthma attack, diabetic attack or any other ailment that may need immediate attention.

In yet another embodiment, the information may be sent to a backend server, where the data may be stored for later retrieval or analysis by the user or a third-party trusted entity for further processing and analysis. For example, the data may be stored by a hospital for the user.

It should be appreciated that the specific steps illustrated in FIG. 10 provide a particular method of switching between modes of operation, according to an embodiment of the present invention. Other sequences of steps may also be performed accordingly in alternative embodiments. For example, alternative embodiments of the present invention may perform the steps/blocks outlined above in a different order. To illustrate, a user may choose to change from the third mode of operation to the first mode of operation, the fourth mode to the second mode, or any combination therebetween. Moreover, the individual steps/blocks illustrated in FIG. 10 may include multiple sub-steps that may be performed in various sequences as appropriate to the individual step. Furthermore, additional steps/blocks may be added or removed depending on the particular applications. One of ordinary skill in the art would recognize and appreciate many variations, modifications, and alternatives of the process.

Figure 11:
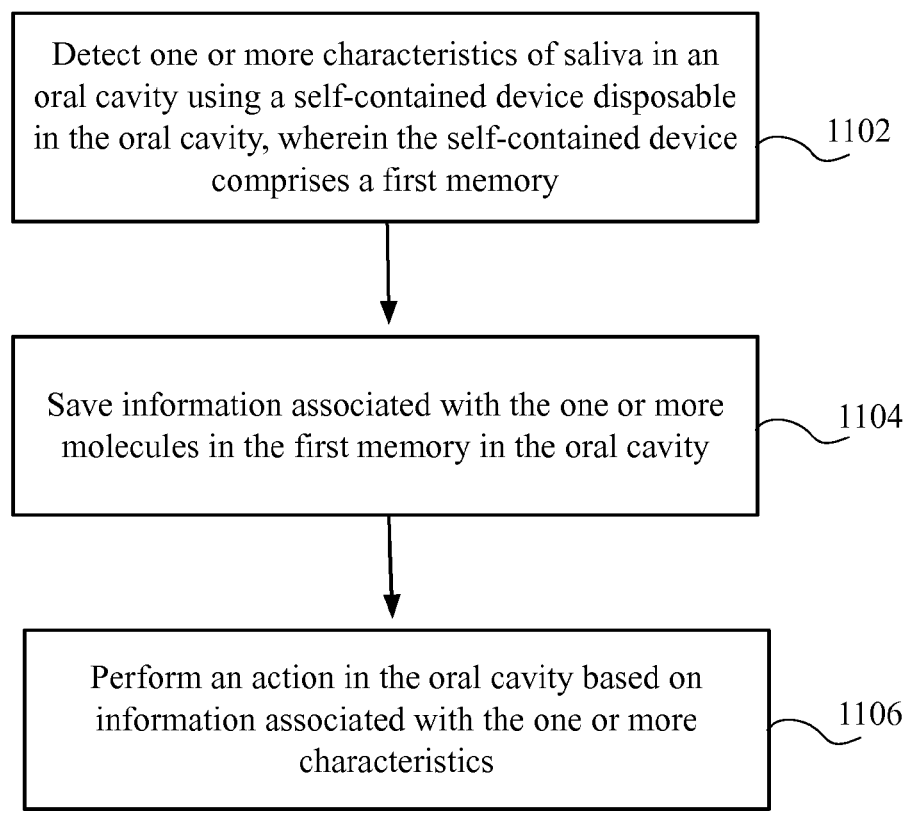
FIG. 11 is an example flow diagram illustrating detecting one or more characteristics of saliva in the oral cavity according to one example embodiment of the disclosure.

FIG. 11 is an example flow diagram illustrating detecting one or more characteristics of saliva in the oral cavity according to one example embodiment of the disclosure. As described herein, a being may refer to a human being or an animal. The steps performed in reference to FIG. 11 may be performed using a processor, hardware or analog and/or digital logic, analog and/or digital sensor logic, or any combination thereof. In certain implementations, certain components described in reference to FIG. 22 may be used in performing steps/blocks described in FIG. 11.

Step 1102 of FIG. 11 is similar to step 902 of FIG. 9, wherein, components of the device, detect one or more characteristics of the saliva in an oral cavity using a self-contained device disposable in the oral cavity, wherein the self-contained device comprises a first memory.

Similarly, step 1104 of FIG. 11 is similar to step 904 of FIG. 9, wherein components of the device save information associated with the one or more molecules in the first memory in the oral cavity.

At step 1106, component of the device, may further perform an action in the oral cavity based on information associated with the one or more characteristics. For example, the device may release a small dose of medication for a condition detected based on detecting one or more characteristics in the oral cavity. For instance, in response to detecting an indication of a heart attack, the device may be configured to release a small dose of Asprin®, NSAID or any other medication to prevent further deterioration of the beings condition. Components of the device may take other remedial steps in response to detecting an asthma attack.

In certain implementations, the device may also be configured to provide other feedback to the user, such as provide a low voltage and current shock or provide a vibration. For example, the device may provide feedback to the user in response to detecting a stress marker, such as cortisol in the saliva beyond a certain threshold. In some instances, the feedback may remind the user to relax or avoid the stressful activity. The device may be further configured to continually provide feedback to the user, as long as the user continues to engage in the stressful activity to discourage such activities.

It should be appreciated that the specific steps illustrated in FIG. 11 provide a particular method of switching between modes of operation, according to an embodiment of the present invention. Other sequences of steps may also be performed accordingly in alternative embodiments. For example, alternative embodiments of the present invention may perform the steps/blocks outlined above in a different order. To illustrate, a user may choose to change from the third mode of operation to the first mode of operation, the fourth mode to the second mode, or any combination therebetween. Moreover, the individual steps/blocks illustrated in FIG. 11 may include multiple sub-steps that may be performed in various sequences as appropriate to the individual step. Furthermore, additional steps/blocks may be added or removed depending on the particular applications. One of ordinary skill in the art would recognize and appreciate many variations, modifications, and alternatives of the process.

Figure 12:
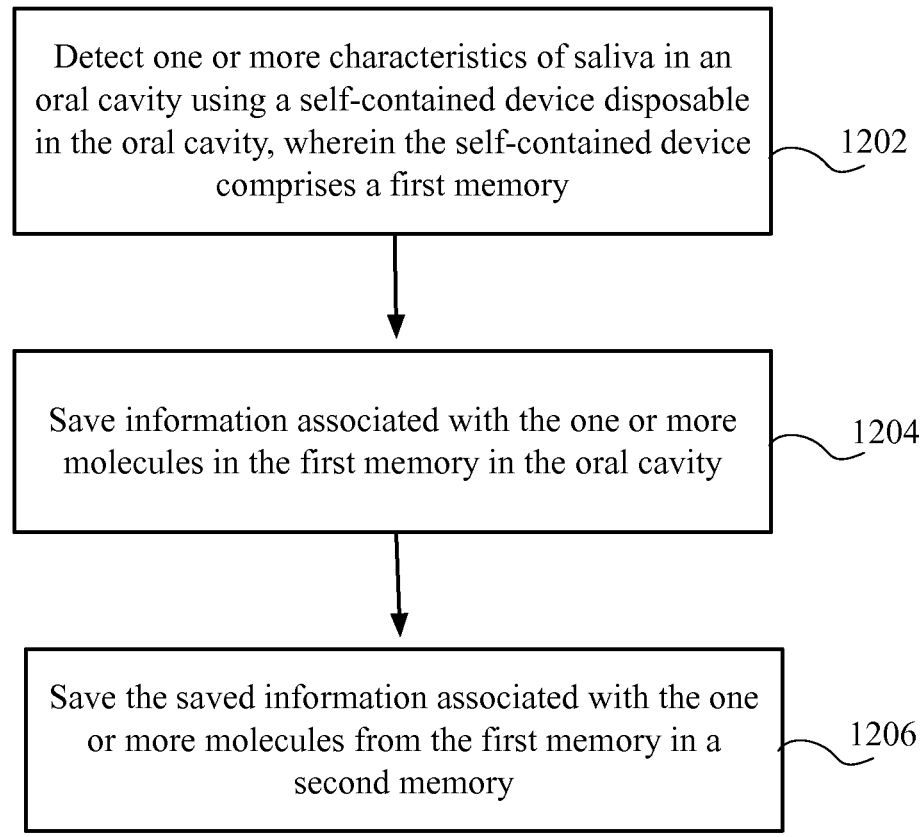
FIG. 12 is an example flow diagram illustrating detecting one or more characteristics in the oral cavity according to one example embodiment of the disclosure.

FIG. 12 is an example flow diagram illustrating detecting one or more characteristics in the oral cavity according to one example embodiment of the disclosure. As described herein, a being may refer to a human being or an animal. The steps performed in reference to FIG. 12 may be performed using a processor, hardware or analog and/or digital logic, analog and/or digital sensor logic, or any combination thereof. In certain implementations, certain components described in reference to FIG. 22 may be used in performing steps/blocks described in FIG. 12.

Step 1202 of FIG. 12 is similar to step 902 of FIG. 9, wherein, components of the device, detect one or more characteristics associated with the saliva in an oral cavity using a self-contained device disposable in the oral cavity, wherein the self-contained device comprises a first memory.

Similarly, step 1204 of FIG. 12 is similar to step 904 of FIG. 9, wherein components of the device save information associated with the one or more characteristics of the saliva in the first memory in the oral cavity.

At step 1206, component of the device, may save the saved information associated with the one or more molecules from the first memory in a second memory.

In some implementations, the first memory may be a volatile memory and the second memory may be non-volatile memory. The first memory may be used as a temporary store before the data is further processed and/or stored in the second memory for longer periods of storage.

In certain embodiments, the information associated with the one or more characteristics is stored for further processing and taking further actions at a later point in time. In certain embodiments, the information may be logged for retrieval by another system at a later point in time for further analysis. For example, the device may store detection of certain characteristics determined to fit a certain criteria (e.g., type, time of the day, frequency, etc.) with a timestamp for later retrieval and analysis.

It should be appreciated that the specific steps illustrated in FIG. 12 provide a particular method of switching between modes of operation, according to an embodiment of the present invention. Other sequences of steps may also be performed accordingly in alternative embodiments. For example, alternative embodiments of the present invention may perform the steps/blocks outlined above in a different order. To illustrate, a user may choose to change from the third mode of operation to the first mode of operation, the fourth mode to the second mode, or any combination therebetween. Moreover, the individual steps/blocks illustrated in FIG. 12 may include multiple sub-steps that may be performed in various sequences as appropriate to the individual step. Furthermore, additional steps/blocks may be added or removed depending on the particular applications. One of ordinary skill in the art would recognize and appreciate many variations, modifications, and alternatives of the process.

Figure 13:
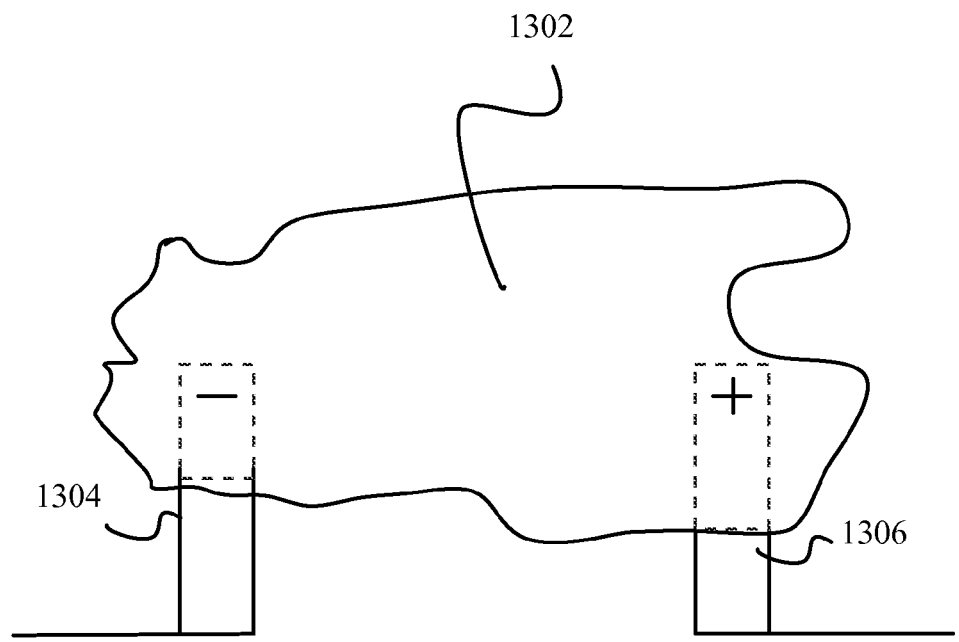
FIG. 13 is an example illustration for determining characteristics associated with saliva, according to some aspects of the disclosure.

FIG. 13 is an example illustration for determining characteristics associated with saliva, according to some aspects of the disclosure. FIG. 13 may represent saliva 1302 in an oral cavity with a plurality of electrodes (1304 and 1306) in contact with the saliva 1302. The saliva 1302 may conduct electricity between the electrodes. In one implementation, the conductivity of the saliva at any given point in time may be used in determining various characteristics associated with the saliva.

The electrodes (1304 and 1306) may be placed in several different locations in or on the housing for the device. For example, in FIG. 16, each of the barbell ends for the piercing may act as an electrode. Similarly, the electrodes may be placed at different locations on the device with non-conductive materials between the two electrodes.

Figure 14:
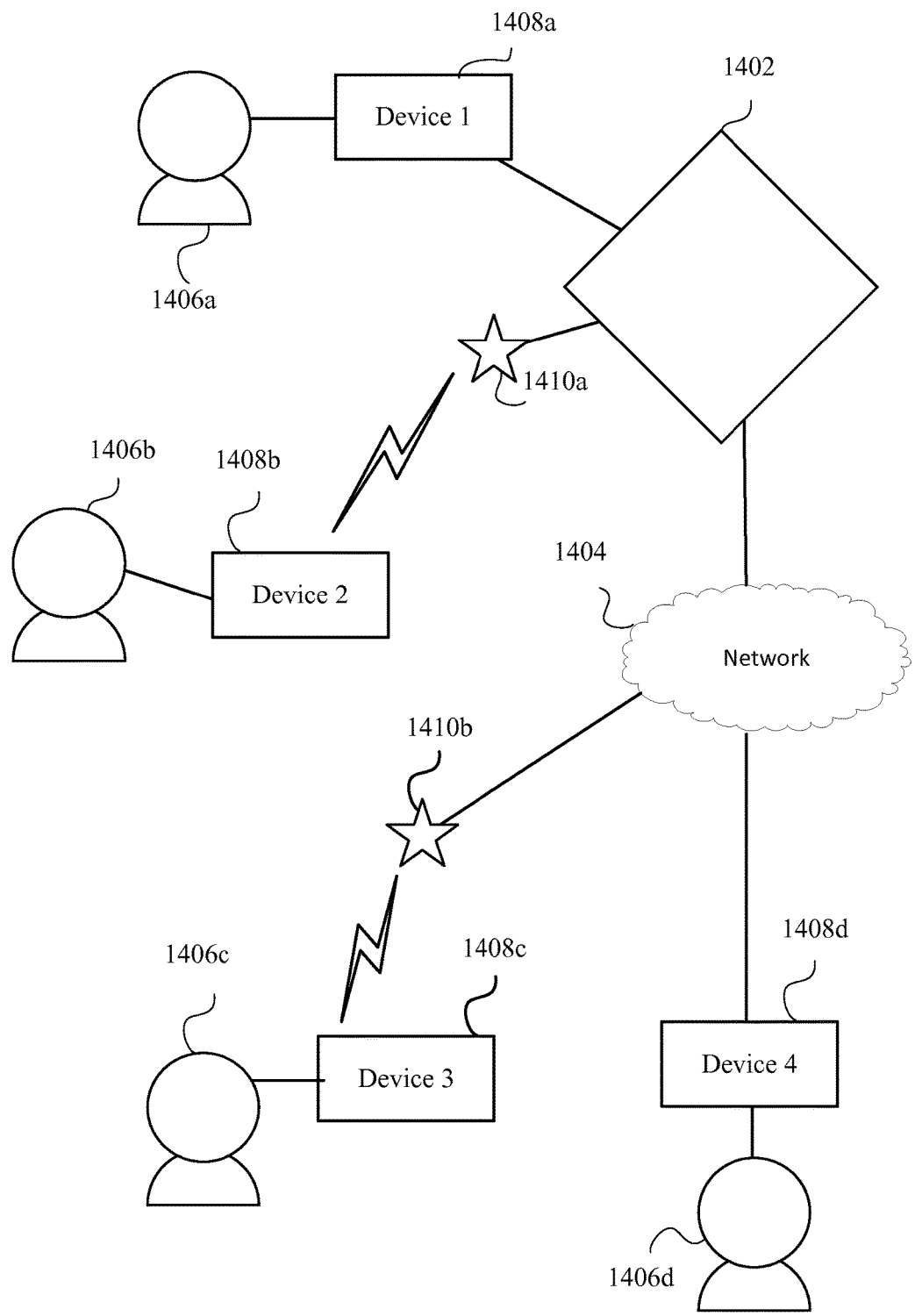
FIG. 14 is an example system figure for a simplified crowdsourcing system, wherein the server receives data from a plurality of devices.

FIG. 14 is an example system figure for a simplified crowdsourcing system, wherein the server 1402 receives data from a plurality of devices (1408*a*, 1408*b*, 1408*c*, and 1408*d*). The server may be configured to wirelessly or through a wired connection receive information from the plurality of devices. The server 1402 may comprise several components similar to the components described with reference to FIG. 22, for receiving information, processing information, storing information, communicating information and performing several other functions for carrying out embodiments of the disclosure described herein.

As shown in FIG. 14, several users (1406*a*, 1406*b*, 1406*c* and 1406*d*) may use a device (1408*a*, 1408*b*, 1408*c*, and 1408*d*, respectively) disposable in the oral cavity, wherein the self-contained device comprises a first memory. The first memory may be a volatile or non-volatile memory for temporarily storing information detected by the device. The devices may wirelessly or through a wired connection send information to the server 1402. In some instances, the devices may send information through intermediary access points (1410*a*, 1410*b*) and/or a series of computer systems and routers placed in a network 1404 to the server 1402. In some embodiments the server 1402 is not a dedicated server, but resources associated with a server allocated from a plurality of servers placed inside a cloud service.

In some instances, the server 1402 may be operated by a research center for drawing inferences from data received from a plurality of devices. In certain implementations, the plurality of devices 1408*a*, 1408*b*, 1408*c* and 1408*d* and/or the server 1402 may be configured to anonymize the data before transmitting and storing the data for further processing. For example, anonymizing the data may comprise removing any information associated with the data that may uniquely identify any user from the plurality of users. For example, anonymizing the data may comprise, removing the user name, birth month and day, device identifier (e.g., IP address. MAC address), location, etc.

In some instances, the server 1402 may further process the data received from the plurality of devices to draw inferences between certain molecules, analytes and/or characteristics detected from the oral cavity and certain conditions for the user. For example, in one simplified example, a device may detect particular characteristics associated with the saliva at a particular time or period of time. In addition, during the same period of time the user may provide information regarding a certain condition associated with the user. For example, the user may indicate that the user is very angry. Additional information regarding the user, such as age, height, and/or body weight may be used in coloring the information received from the user device.

The server 1402 may collect several samples of data comprising similar information from the same device and several other devices. In some instances, the server 1402 may receive thousands of data points. For example, components of the server 1402 may be configured to draw inferences between the detected characteristics for the saliva and anger using the several samples of data received from several devices over a period of time. Furthermore, as more devices provide more associations over time, the server 1402 can continually improve the associations between certain characteristics of the saliva and the anger.

Once the server 1402 has enough information to draw acceptable inferences, the server 1402 may update the devices with indicators that alert the user of the condition or the onset of the condition. For example, the device upon detection of the characteristics that have been observed in the past before the onset of an anger burst may alert the user through a feedback loop (e.g., vibration) that the user is currently gravitating towards an uncontrollable anger episode, prompting the user to recede from the trigger event resulting in such an occurrence.

It should be noted, that anger is provided as an example and many other conditions or ailments may be detected and controlled. For example, the dangerous glucose level in the saliva or the stress markers for a user may be detected by detecting various combinations of molecules, analytes and various characteristics associated with the user.

In some instances, the device used for a user may also be programmed and personalized for a user, based on previous data associated with the user. In such instances, the data may not be anonymized, but stored separately. In certain instances, the data may be stored with additional encryption and privacy disclosures to the user.

Figure 15:
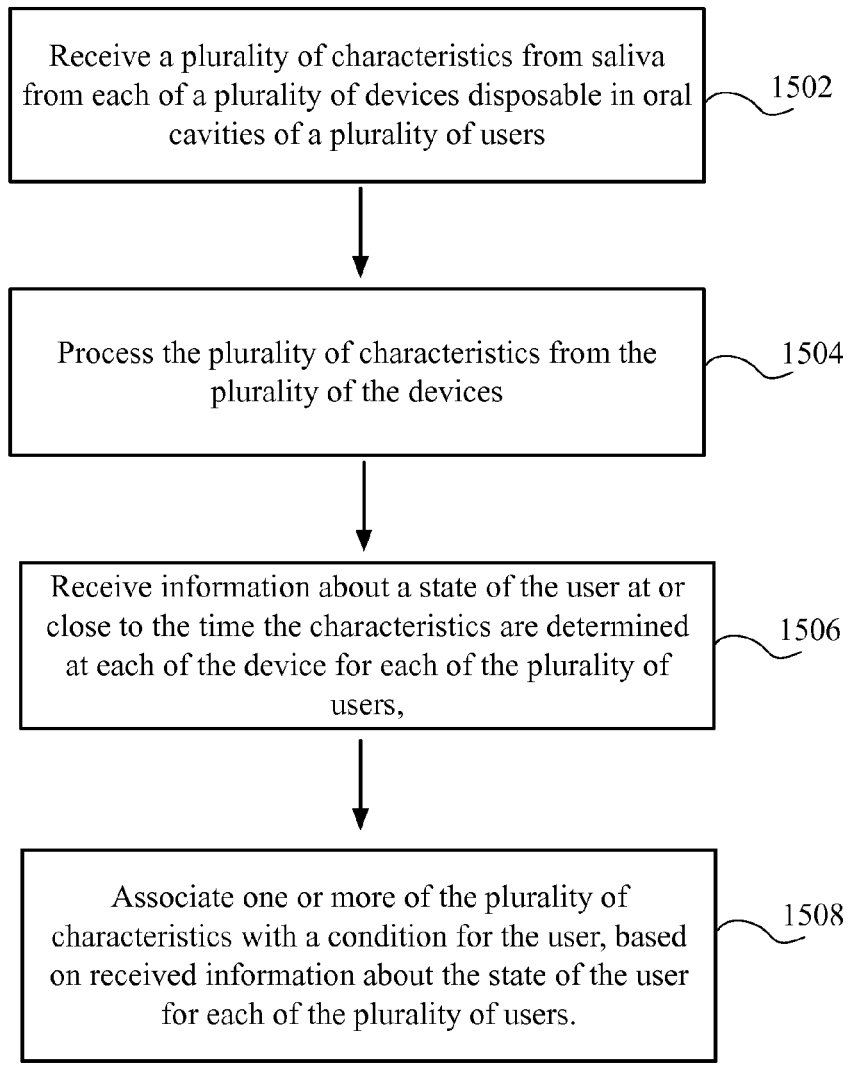
FIG. 15 is an example flow diagram for illustrating a method performed by a crowdsourcing server, according to certain aspects of the disclosure.

FIG. 15 is an example flow diagram for illustrating a method performed by a crowdsourcing server, according to certain aspects of the disclosure. As discussed previously, the crowdsourcing server may not be a dedicated server, but an instance of resources associated with the crowdsourcing functions operating on one of a plurality of servers temporally allocated for the task. For instance, the crowdsourcing function may be performed by an operating instance (such as a virtual machine or container) allocated on a cloud. The crowdsourcing server may operate using components similar to the components described with respect to FIG. 22.

At step 1502, components of the server, receive a plurality of characteristics from saliva from each of a plurality of devices disposable in oral cavities of a plurality of users. In some instances, the server may also receive information associated with regard to the molecules and/or analytes detected by the devices in addition to the characteristics.

At step 1504, the server may process the information received from the plurality of devices. At step 1506, the server may receive information about a state of the user at or close to the time the characteristics are determined at each of the device for each of the plurality of users. For example, the user may be provided an interface to provide information regarding the user's condition, such as the user is angry, hungry, stressed out, or is having a migraine.

At step 1506, components of the server may associate one or more of the plurality of characteristics with a condition for the user, based on the received information about the state of the user for each of the plurality of users.

It should be appreciated that the specific steps illustrated in FIG. 15 provide a particular method of switching between modes of operation, according to an embodiment of the present invention. Other sequences of steps may also be performed accordingly in alternative embodiments. For example, alternative embodiments of the present invention may perform the steps/blocks outlined above in a different order. To illustrate, a user may choose to change from the third mode of operation to the first mode of operation, the fourth mode to the second mode, or any combination therebetween. Moreover, the individual steps/blocks illustrated in FIG. 15 may include multiple sub-steps that may be performed in various sequences as appropriate to the individual step. Furthermore, additional steps/blocks may be added or removed depending on the particular applications. One of ordinary skill in the art would recognize and appreciate many variations, modifications, and alternatives of the process.

Figure 16:
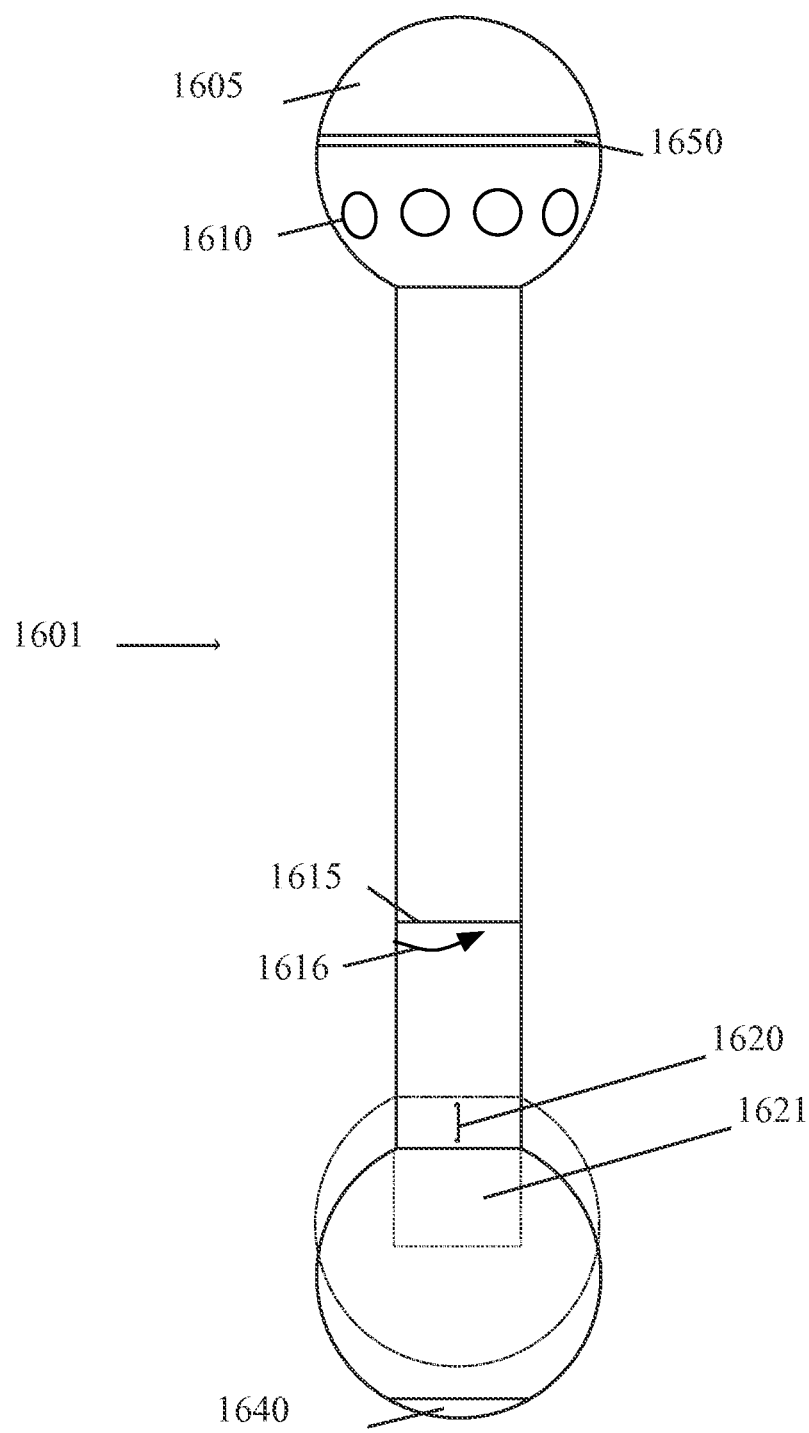
FIG. 16 illustrates a perspective view of an embodiment of a device, a barbell-shaped stud that can be worn embedded in or pierced through mouth tissue.

FIG. 16 illustrates an embodiment of the invention as a perspective view of a barbell-shaped jewelry or stud. The stud can include without limitation barbell-shaped enclosure 1601, which can be capable of resisting deformation under repeated physical stress. Examples of materials barbell-shaped enclosure 1601 could be comprised of include, but are not limited to, metal, plastic, glass, composites, and/or other materials and/or combinations of these materials. In this embodiment, barbell-shaped enclosure 1601 may be the shape of a cylinder joining larger-diameter spherical shapes at either end along the long center axis, and may be of appropriate size to pierce through a lip and/or tongue of a mouth, and/or other size. In alternate embodiments, barbell-shaped enclosure 1601 might have different shapes and/or sizes, including without limitation disk-shaped and/or asymmetrically-shaped ends instead of spherical ends, a larger and/or smaller size, an asymmetrical shape, a longer or shorter cylinder and/or other shapes and/or sizes. In other embodiments, barbell-shaped enclosure 1601 might be shaped to grip or contact surfaces of the mouth in other ways, such as one or more oblong end shapes instead of spherical ends to allow easier rotation of the ends and/or the device, and/or one or more stylus point ends for writing and/or doing finer movements. This embodiment may be implemented using one or more components as described in FIG. 22 and/or in previous paragraphs. In this embodiment of the invention, touch sensor device 1605, a pressure sensor device 1650, signal light 1640, and an electrical stimulator device 1610 fit into the surface of barbell-shaped enclosure 1601. In this embodiment of the invention, a rotation sensor device 1615 bisects the cylinder, allowing for a twisting and/or rotating 1616 of the ends of the device along the long center axis and compression sensor device 1621, which allows the housing a compression (and/or expansion) 1620 (the motion might also be used to generate power for power device), fits into the surface of barbell-shaped enclosure 1601. In other embodiments of the invention, these devices might be differently-located, omitted, and/or duplicated at multiple locations, such as having an instance of touch sensor device 1605 at both ends of the device, having rotation sensor device 1615 closer to one of the ends of the cylinder section of barbell-shaped enclosure 1601, or other differences.

Other sensors, such as bio-molecular sensors may be placed or coupled to various locations of the bar-bell piercing. In addition, as described in FIG. 13, a plurality of electrodes may be placed on the ends of the bar-bell of the piercing or any other location. Such bio-sensors or electrodes may be exposed such that they have direct contact to the saliva in the oral cavity.

In this embodiment of the invention, processor 2210 can be a small Arduino-compatible microcontroller, and communications subsystem 2230 can be a Bluetooth radio device with antenna.

In this embodiment of the invention, working memory 2235 can be a flash-memory integrated circuit.

In this embodiment of the invention, multiple one or more input devices 2215 can be: touch sensor device 1605, a touchpad sensor; rotation sensor device 1615, a rotation sensor; compression sensor device 1621, a compression-sensing sensor; pressure sensor device 1650, a microphone sensor; and two internal accelerometer and/or gyroscope sensor devices (one in each end of the device).

In this embodiment of the invention, power device 2260 can be a battery.

In this embodiment of the invention, one or more output devices 2220 are: electrical stimulator device 1610, an electrical stimulator with two or more electrodes; signal light 1640, an LED light; and two internal mechanical wave generator devices (one in each end of the device), vibration-producing devices.

In this embodiment of the invention, storage device 2225 can be a flash-memory integrated circuit.

In this embodiment of the invention, operating system 2240 can be machine code that can be read by processor 2210 and can guide the functioning of device 2200.

In this embodiment of the invention, application 2245 can be code that can be read by processor 2210 and can guide additional functioning of device 2200.

Using communications subsystem 2230, the embodiment of the invention illustrated in FIG. 16 might be in communication with remote devices and/or similar devices, including, but not limited to other devices in and/or on and/or near the body of the wearer (such as a head-mounted display device, a wrist-mounted display device, a pacemaker device, an insulin pump device, a mobile device, a network device, a wireless device, and/or a home automation device), and/or remote devices, and/or networks of devices, and/or devices. Merely by way of example, device 2200 might allow the wearer, by interacting with one or more input devices 2215, to communicate to a remote device such as a head-mounted visual display device to control a cursor or change a selection presented in the visual display device.

Figure 17:
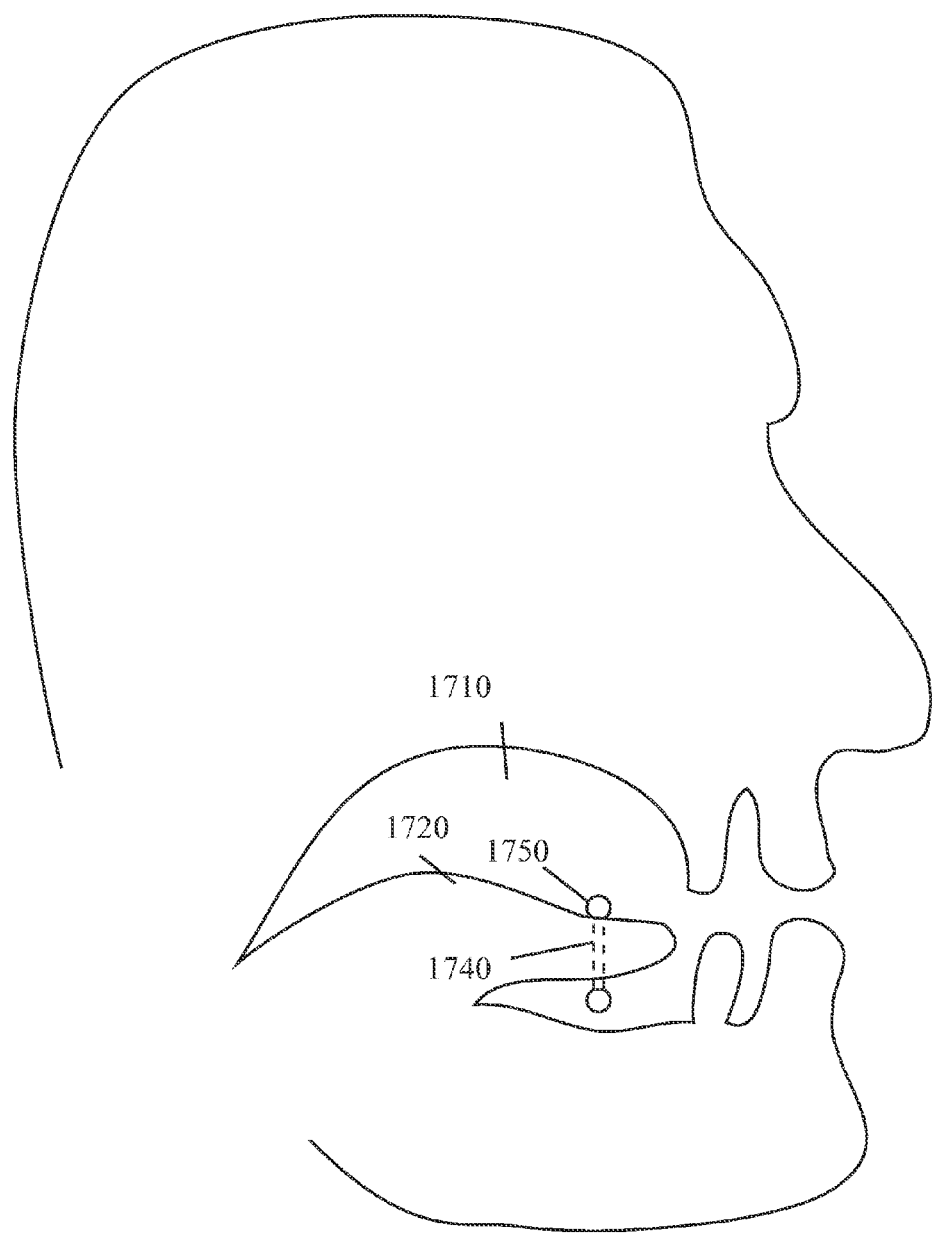
FIG. 17 is a perspective view of a cross section of a human head, showing the positioning of the device as embodied in FIG. 16.

FIG. 17 is a perspective view of a cross section of a head (in this case a human head), showing one possible position of device 1750 (the device described in FIG. 2 and preceding paragraphs).

In FIG. 17, device 1750 can be anchored through and/or in one or more pierced site(s) 1740 around and/or in an oral cavity 1710 of the wearer, through and/or in a tongue 1720. In this embodiment the wearer is a human, but in other embodiments and/or usages, the wearer might be any kind of animal. In other embodiments and/or usages, positioning of device 1750 might be in and/or through one or more pierced sites 1740 in and/or through one or more other locations and/or one or more orientations around and/or in and/or through and/or under the tissue surrounding and/or near oral cavity 1710 (such as through a lip), and/or anywhere around and/or in and/or through and/or within the body and/or form of a user. Tongue 1720 (and/or other tissues of the mouth and/or body) could have one or more pierced sites 1740 and/or one or more one or more devices 1750 and/or other embodiments of the invention.

Oral cavity 1710 and/or tongue 1720 could also have multiple one or more pierced sites 1740 and/or multiple one or more devices 1750 and/or other devices.

Using communications subsystem 2230, device 1750 might be in communication with remote devices and/or similar devices, including, but not limited to other devices in and/or on and/or near the body of the wearer (such as a head-mounted display device, a wrist-mounted display device, a pacemaker device, an insulin pump device, a mobile device, a network device, a wireless device, and/or a home automation device), and/or remote devices, and/or networks of devices, and/or devices. Merely by way of example, device 1750 might allow the wearer, by interacting with one or more input devices 2215, to control a cursor or change a selection presented in the visual display of a separate head-mounted display device and/or provide feedback to the environment of oral cavity 1710 about the remote action in the remote device in the form of a vibratory or haptic vibration within device 1750.

In one embodiment, the barbell-shape of barbell-shaped enclosure 1601 may be advantageous since it houses and protects the device and resists deformation under physical stress and keeps the device in pierced site 1740.

In this embodiment of the invention, from pierced site 1740, the input devices 2215 of device 1750 might observe tongue 1720, the tissues of the mouth, and/or the environment of oral cavity 1710 (and/or beyond): touch sensor device 1605, a touchpad sensor device, can sense touch (as device 1750 moves with tongue 1720 and comes in contact with mouth tissues (such as the gums, teeth, lips, floor of the mouth, upper palate, and the like) and/or other objects and/or devices); rotation sensor device 1615, a rotation sensor device, can sense rotation of the ends the device (this could be accomplished using the tongue or other tissues of the mouth, or by the fingers, reaching into or up to the mouth, and could, merely by way of example, be used as an on/off switch for the device); compression sensor device 1621, a compression-sensing sensor device, can sense compression (and/or expansion) 1620 (and compression sensor device 1621 can be returned to its resting state by a spring, or the like) of the cylinder of device 1750 (such as by flattening and/or fattening of tongue 1720, and/or by pressing or pulling on the ends of device 1750 in other ways); pressure sensor device 1650, a microphone sensor device, can sense sound, such as vocalizations and/or sub-vocalizations, breathing, and other sounds that come into oral cavity 1710; and two internal accelerometer and/or gyroscope sensor devices (one in each end of the device), orientation and/or acceleration sensor devices, can sense the orientation and/or acceleration of device 1750 (which can be affected by actions of pierced site 1740, and/or tongue 1720).

Other sensors, such as bio-molecular sensors may be placed or coupled to various locations of the bar-bell piercing. In addition, as described in FIG. 13, a plurality of electrodes may be placed on the ends of the bar-bell of the piercing or any other location. Such bio-sensors or electrodes may be exposed such that they have direct contact to the saliva in the oral cavity.

In this embodiment of the invention, tongue 1720, the tissues of the mouth, and/or the environment of oral cavity 1710 (and/or beyond) might also observe device 1750, including output devices 2220 of device 1750: electrical stimulator device 1610 can create sensation via electric current; signal light 1640 can create light and light beams; and the two internal mechanical wave generator devices (one in each end of the device), can create vibration and/or vibration differentials and/or one or more stereo vibration fields and/or haptic fields and/or patterns.

In this embodiment of the invention, the dexterity, and/or communication abilities of the mouth can now be used for, among other things, fine control, interaction, and exchange of information to and/or from and/or through device 1750.

Using one or more input devices 115, some embodiments of the invention might observe and act on analog input from the environment of the mouth and/or entering the environment of the mouth, such as a material sensor device being used to monitor and/or analyze and/or report blood chemical levels, gas levels in the breath, and/or chemical makeup of food ingested of and/or by the user.

Figure 18:
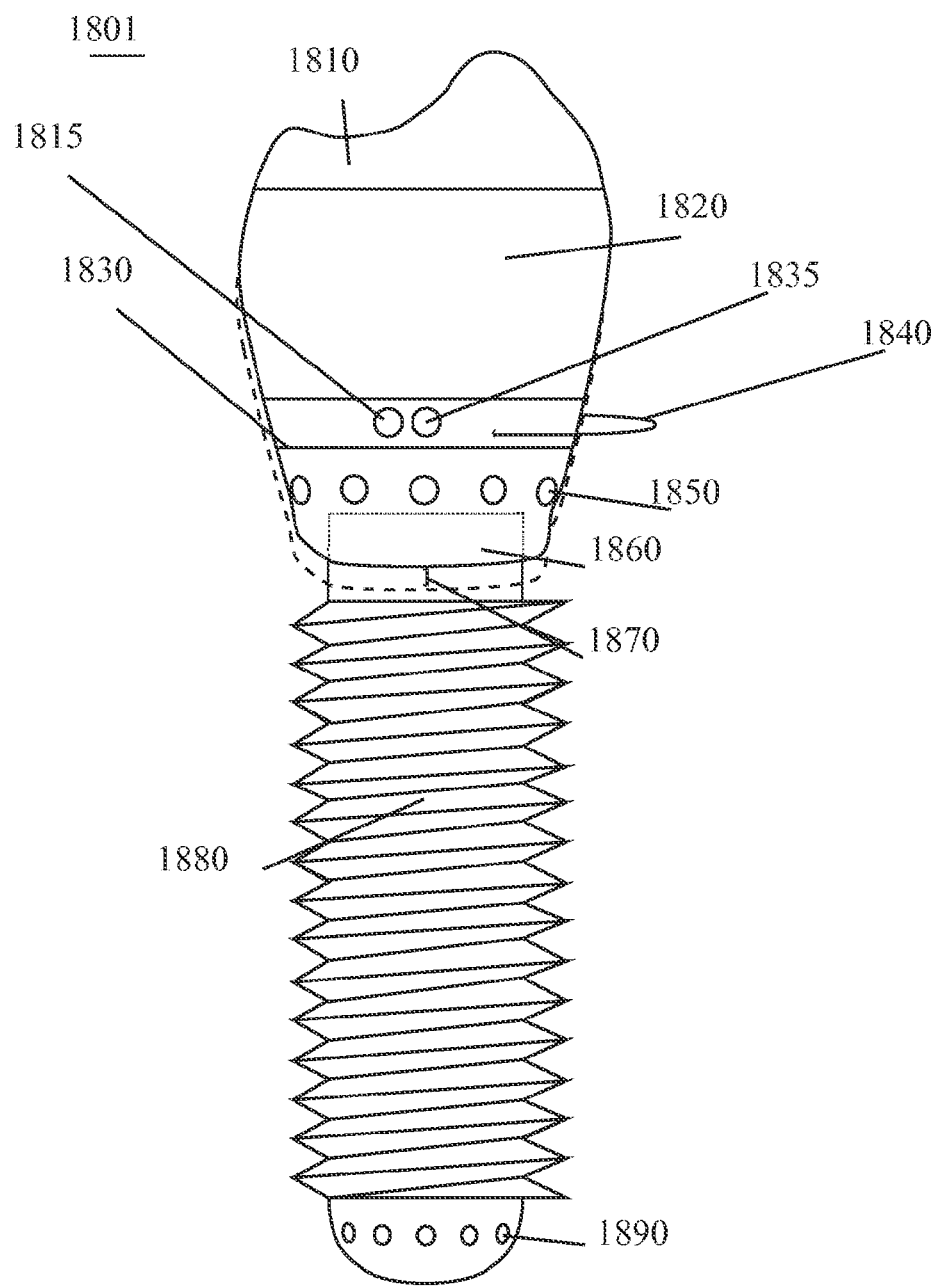
FIG. 18 is a perspective view of a tooth-implant embodiment of the device.

FIG. 18 is a perspective view of a tooth-implant shaped enclosure, according to another embodiment of the present invention. Tooth implant shaped enclosure 1801 may be implemented using one or more components as described in FIG. 1 and/or in previous paragraphs.

In this embodiment, tooth implant shaped enclosure 1801 has a tooth-shaped enclosure 1810 of ceramic or other material that houses and protects the device. Tooth-shaped enclosure 1810 looks similar to a tooth or teeth. In other embodiments, tooth-shaped enclosure 1810 might mimic, partially mimic, and/or not mimic other structures, and/or have a different shape and/or shapes.

Tooth-shaped enclosure 1810 may house touch sensor device 1820 (a touch-sensing device, such as a touchpad, which can wrap around tooth shaped enclosure 1810), rotation sensor device 1830 (that can sense twisting or rotating 1840), compression sensor device 1860 (that can sense compression (and expansion) 1870), electrical stimulator device 1850, and may have tooth implant anchor 1880, which may also have anchor electrical stimulator device 1890. In other embodiments, tooth implant shaped enclosure 1801 might lack tooth implant anchor 1880, and, instead connect to an external tooth implant via an implant connection socket.

Figure 19:
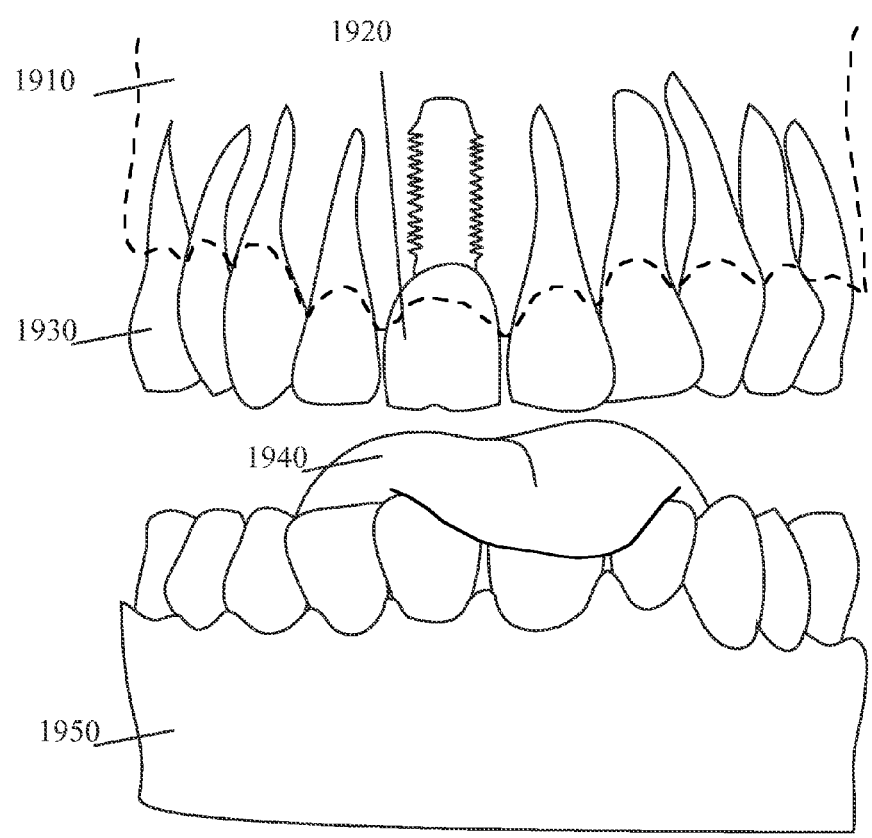
FIG. 19 is a perspective view of the teeth, gums and tongue of a human mouth, showing the position of the device as embodied in FIG. 18.

FIG. 19 is a perspective view inside a mouth, with teeth (including tooth 1930), upper gums/maxilla 1910, lower gums/mandible 1950 and tongue 1940, with upper gums/maxilla 1910 hidden to show the full teeth. FIG. 19 shows the device, as embodied in FIG. 18, worn in one possible tooth implant location 1920 in the upper gums/maxilla 1910. This embodiment may be implemented using one or more components as described in FIG. 1 and/or in previous paragraphs.

In this embodiment of the device, one or more input devices 115 may include without limitation: one or more touch sensor devices 1820 (built into the surface of the housing) that responds to touch input and/or can create 'mouse'-type positioning, tap, pressure, coverage and/or touch-related data; compression sensor device 1860 inside the housing that responds to compression (and expansion) 1870 along the length of the housing; a rotation sensor device 1830 in the housing that can sense twisting or rotating 1840 the two ends of the device; a pressure sensor device 1835 that responds to air pressure; and one or more internal accelerometer and/or gyroscope sensor devices, orientation and/or acceleration sensor devices that can sense the orientation and/or acceleration of tooth implant shaped enclosure 1801.

In this embodiment of the device, one or more output devices 120 may include without limitation: a mechanical wave generator device that can be a vibration device and/or or a speaker device (a vibration device creates vibration in the device using a vibration motor device or other vibration-causing device, a speaker device creates sound waves from the device by creating movement using a speaker or other movement-creating device); signal light 1815, a light device (a light device can display one or more lights and/or beams of light) that displays a light; an electrical stimulator device 1850 that can create sensation in the wearer via electric shocks from electrodes, and/or anchor electrical stimulator device 1890, that can create sensation in the wearer via electric shocks from electrodes. The actions of the output devices 120 can be perceived by the user and/or others.

FIG. 19 is a perspective view of the teeth, gums and tongue of a human mouth, showing the position of the device as embodied in FIG. 18. This embodiment may be implemented using one or more components as described in FIG. 1 and/or in previous paragraphs. In this embodiment of the invention, the device can be worn in a user's mouth, such as in FIG. 19, embedded in upper gums/maxilla 1901, or lower gums/mandible 1950 by the titanium (or other, suitable material) threads of tooth implant anchor 1880. In this placement of the device, one or more input devices 115 (such as touch sensor device 1820, compression sensor device 1860, rotation sensor device 1830, pressure sensor device 1835, and the internal accelerometer and/or gyroscope sensor device) can be manipulated by the tongue 1940, lips, other parts of the mouth and/or by other means (such as movement of the head or jaw).

Figure 20:
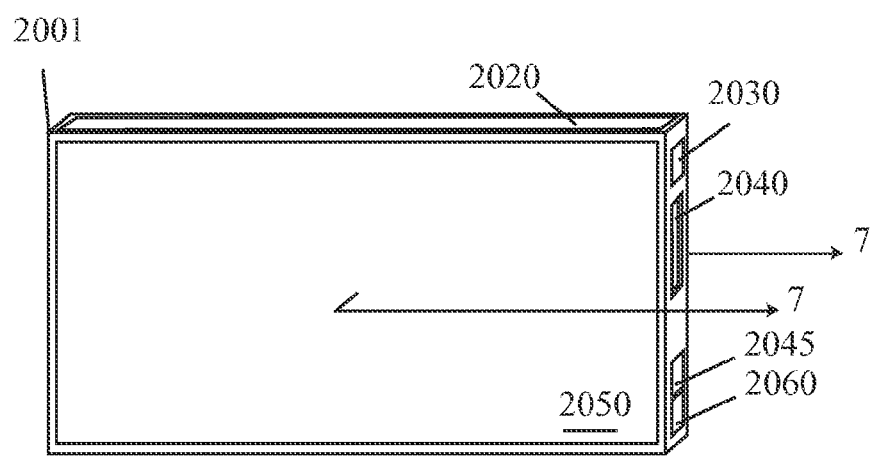
FIG. 20 is a perspective view of a dental bridge embodiment of the device.

FIG. 20 is a perspective view of a dental bridge-shaped enclosure, according to an embodiment of the present invention. This embodiment may be implemented using one or more components as described in FIG. 22 and/or in previous paragraphs. The dental bridge-shaped enclosure includes without limitation bridge enclosure 2001 of metal, pyrex, plastic, or other material or materials that houses and protects the device. Bridge enclosure 2001 can be affixed to the teeth of the mandible or maxilla via regular bridge attachment methods or as part of a dental retainer, such as a Hawley retainer.

Bridge enclosure 2001 can allow one or more input devices 115 to observe the environment around the device and one or more output devices 120 to act (directly or indirectly) on the environment around bridge enclosure 2001, while sealing and protecting device 100 from damage.

In this embodiment of the invention, one or more input devices 115 may include: a touch sensor device 2050 (built into the surface of the housing) that can respond to touch input and/or can create 'mouse'-type positioning, tap, pressure, coverage and/or touch-related data; a compression sensor device 2020 inside the housing; a compression switch 2030; a pressure sensor device 2060 that can respond to air pressure, and an internal accelerometer and/or gyroscope sensor device, orientation and/or acceleration sensor devices that can sense the orientation and/or acceleration of bridge enclosure 2001.

In this embodiment of the invention, one or more output devices 120 may include, but are not limited to: a mechanical wave generator device that can create vibrations from a vibration motor device; a light device that can display a signal light 2040; and a shock device that creates small electric shocks from an electrodes of electrical stimulator device 2045, arrayed on the surface of the device.

In one embodiment input/output device may also include a wave device that may generate and/or detect waves, such as energy waves. In one embodiment, the wave may be an RF wave, acoustic wave, light wave or any other type of wave.

Figure 21:
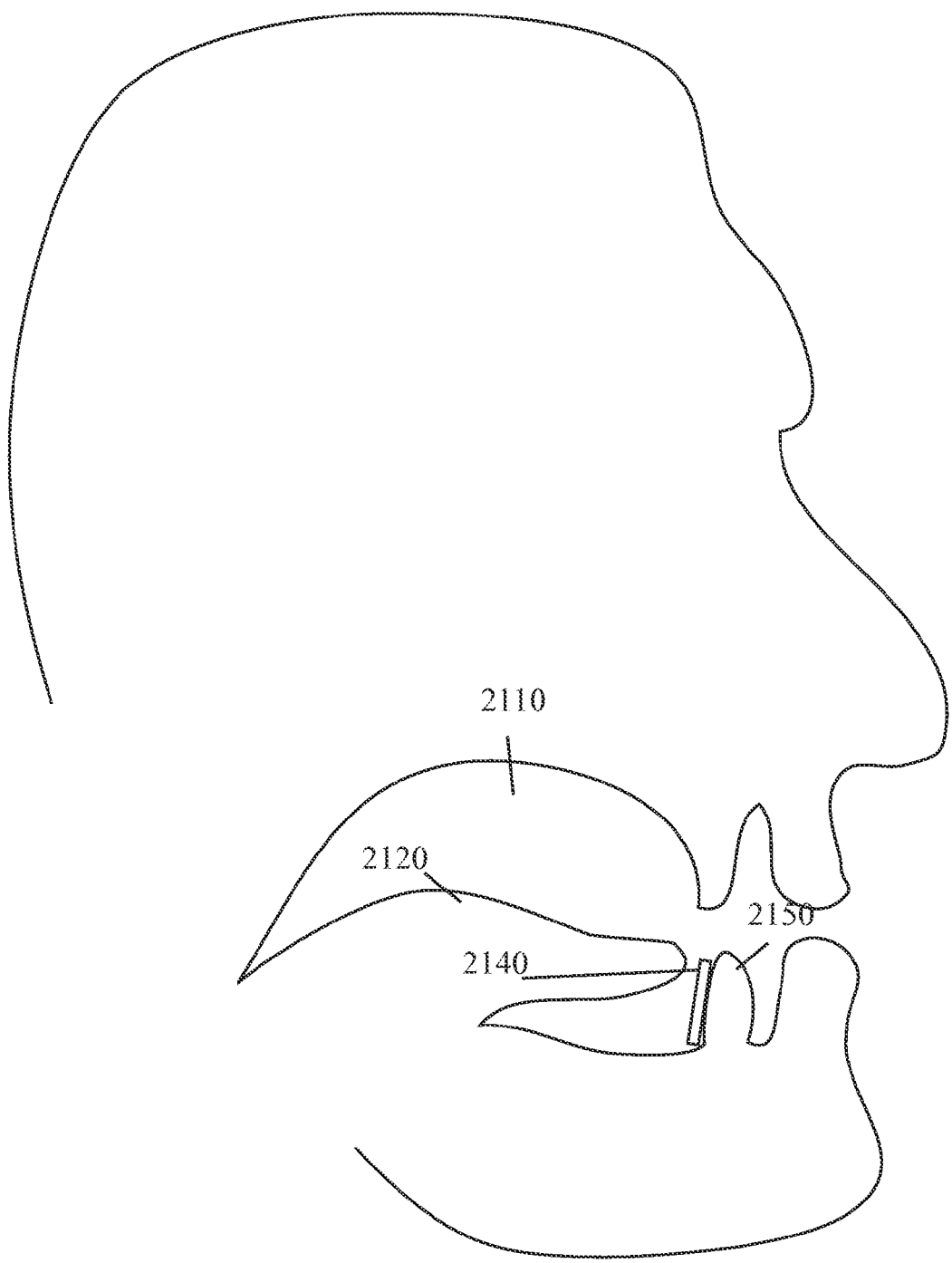
FIG. 21 is a perspective view of a cross section of a human head, showing the positioning of the device as embodied in FIG. 20.

FIG. 21 is a perspective view of a cross section of a human head, cut away to show the oral cavity 2110, the tongue 2120, and the device 2140, as embodied in FIG. 20, worn in one possible location, affixed to the teeth of mandible 2150 in the orientation as indicated by lines 21-7 in FIG. 20. This embodiment may be implemented using one or more components as described in FIG. 1 and/or in previous paragraphs.

In this embodiment, the device can be worn in a user's mouth, such as in FIG. 21, affixed to the teeth of the mandible 2150. In this placement of the device, tongue 2120 can access touch sensor device 2050, and compression sensor device 2020 can be manipulated by the tongue 2120, lips, other parts of the mouth and/or by other means. And the actions of one or more output devices 120 can be perceived by the user and/or others. In regular operation of the device, tongue 2120 can stay in a fairly relaxed position along the mandible and can stay clear of blocking most regular mouth function.

Figure 22:
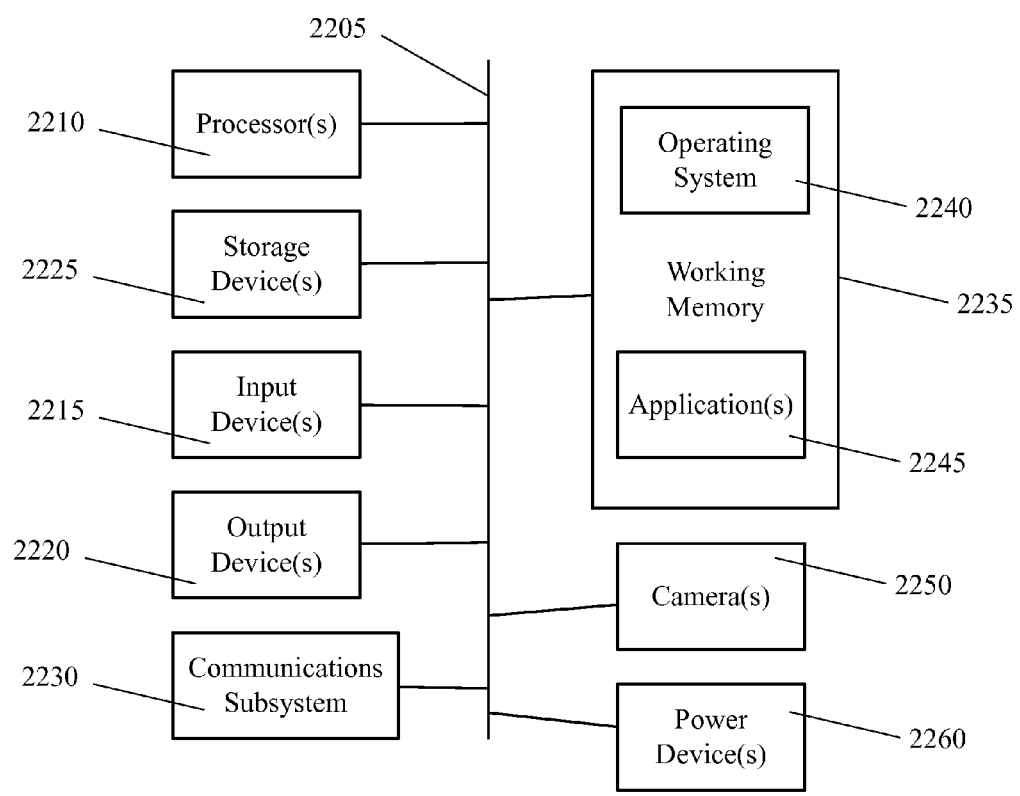
FIG. 22 describes one potential implementation of a computing device, according to certain embodiments of the present disclosure.

FIG. 22 illustrates an exemplary device incorporating parts of the device employed in practicing embodiments of the invention. An exemplary device as illustrated in FIG. 22 may be incorporated as part of the described computerized device below. For example, device 2200 can represent some of the components of a mobile device. A mobile device may be any computing device with an input sensory unit, like a touchpad, and an output unit, like a speaker. The sensory unit may also include sensors for detecting molecules, analytes, substances and characteristics of saliva in the oral cavity. Examples of a device include, but are not limited to, video game consoles, tablets, smart phones, camera devices and any other portable devices suitable for performing embodiments of the invention. However, a device may also include a server, such as a crowdsourcing server described in FIG. 14. FIG. 22 provides a schematic illustration of one embodiment of a device 2200 that can perform the methods provided by various other embodiments, as described herein, and/or can function as the host device, a remote kiosk/terminal, a point-of-sale device, a mobile device, a set-top box and/or a device. FIG. 22 is meant only to provide a generalized illustration of various components, any or all of which may be utilized as appropriate. FIG. 22, therefore, broadly illustrates how individual system elements may be implemented in a relatively separated or relatively more integrated manner. FIG. 22 is an exemplary portable processing device or mobile device that may use components as described in reference to FIG. 22. In some embodiments, only some of the components described in FIG. 22 are implemented and enabled to perform embodiments of the invention. For example, a touchpad device may have one or more touchpads, storage, or processing components along with other components described in FIG. 22.

The device 2200 is shown comprising hardware elements that can be electrically coupled via a bus 2205 (or may otherwise be in communication, as appropriate). The hardware elements may include, but are not limited to, one or more power devices 2260, including without limitation one or more power storage and/or distribution devices (such as a battery) and/or one or more power generation, storage, and distribution devices (such as a combination of power generator, power management device, and a battery). In other embodiments, power and/or data might be distributed via one or more separate buses, or a combination of buses, and/or individual components of device 2200 might have independent or external power device(s) 2260. The hardware elements may include, but are not limited to, one or more processors 2210, including without limitation one or more general-purpose processors and/or one or more special-purpose processors (such as digital signal processing chips, graphics acceleration processors, random number generator and logic for cryptography, and/or the like). The hardware elements may also include one or more signal-creating input devices 2215 which can sense analog input. One or more input devices 2215 can include without limitation a touchpad, sensors, sensor devices), a microphone, a pushbutton, a gyroscope, and/or an accelerometer and/or the like. For example, a microphone might sense the analog input of sound. The hardware elements may also include one or more output devices 2220, which can produce a stimulus to a subject and/or environment and can include without limitation a vibration device, a light device, an electric-shock and/or electrode-array device, devices (exemplary devices discussed in figures and later paragraphs), and/or the like. For example, an electrode-array device might produce a stimulus of an electric shock to a person it might be touching. In addition, hardware elements may also include without limitation one or more cameras 2250, as shown in FIG. 22, for acquiring image content.

In other embodiments one or more input devices 2215 can include, without limitation: movement tracking sensor devices such as an LED/photo-diode tracking device (as found in an optical mouse) and/or more advanced visual-tracking devices, which can be used to observe and report movement information; pressure sensor devices (like a microphone device, piezoelectric devices, and/or an air pressure sensor device), which can be used to observe and report pressure change information such as sound, vocalizations, breathing or physical stress changes; temperature sensor devices (like a thermometer device), which can be used to observe and report body heat, respiration temperature, external temperature, general temperature, or other temperature information; touch sensor devices (like button devices, switch devices, slider devices, bite pressure devices, piezoelectric devices optical touch devices, rotation sensor devices, optical movement tracking devices and touchpad devices), which can be used to observe and report direct physical interaction and movement information and even indirect physical interaction and movement information; air sensor devices (like machine olfaction devices, gas flow monitor devices, and/or chemical identification devices), which can be used to observe and report breathing, temperature, humidity, pressure, gas flow, gas state, and air quality information; material sensor devices (like machine taste devices, chemical sensor devices, salinity sensor devices, blood analysis devices and/or pH sensor devices), which can be used to observe and report chemical makeup information or other physical characteristics of breath, food, saliva, bodily fluids and/or organs; light sensor devices (like photodiode devices, infrared light sensor devices, light meter devices and/or camera devices), which can be used to observe and report light, distance, thickness, color and movement information; acceleration sensor devices (like an accelerometer or a pedometer device) which can be used to observe and report velocity and/or acceleration change and movement force information; and orientation sensor devices (like a compass device, or a digital gyroscope device), which can be used to observe and report orientation and movement information.

The input devices 2215 may also include sensors for detecting molecules, analytes, substances and characteristics of saliva in the oral cavity.

In other embodiments one or more stimulus and/or output devices 2220 can include, without limitation: electrical stimulator devices (like electrode devices, electrode-array devices, and/or shock devices), which can be used to communicate to or stimulate the user and/or others by applying electric current via electrodes to the surrounding environment (such as to the surface of the tongue, to the interior of the mouth, or to and/or into the tissue of an embedding site); light devices (like indicator light devices, infrared light devices, or laser light or laser pointer devices), which can be used to communicate to the user or others and/or illuminate by creating visible, infrared and/or ultraviolet light and/or light beams (and projected beams can be used as pointing devices or projector displays by the user); tactile, actuator, or touch-based vibration devices (like vibration motor devices, and Braille terminal devices), which can be used to communicate to the user or others by creating vibration based feedback and tactile or touchable states; physical release devices (like metered chemical release devices (which could release chemicals), spray devices, dispenser devices, or pill dispenser devices), which can be used to release matter to communicate to and/or or stimulate the user and others by releasing or dispensing matter into the surrounding environment; and mechanical wave generator devices (like speaker devices and/or vibration devices and/or bone-conduction transducer devices), which can be used to communicate to the user and others by creating sound and other mechanical waves.

In other embodiments one or more power devices 2260 could reside apart from the rest of device 2200, including, without limitation, outside any primary enclosure, in a separate enclosure, and/or connected by a tether and/or power transfer device. In other embodiments power may be generated by one or more power devices 2260 from, including, without limitation, interaction with the chemicals in the internal and/or external environment (such as electrical interaction as in a battery, by using an exposed anode and cathode), and/or interaction with the chemicals and/or pressure of the bloodstream of the user, and/or interaction with the external environment and/or functioning of organisms and/or one or more devices hosted within the device (such as with a genetically-engineered biofuel device and/or biofuel organism that generates power from oxygen and glucose in the bloodstream of a wearer), and/or interaction with temperature differences in the external environment (such as by coupling a generator with a Stirling engine or other heat engine), and/or by movement (such as by coupling a generator with a self-winding mechanism of the type as used in a self-winding watch and/or capturing the energy of actions performed on device 2200), and/or by wireless energy transfer (such as by direct induction, resonant magnetic induction or electromagnetic power reception devices (such as RFID tags)).

The device 2200 may further include without limitation (and/or be in communication with) one or more non-transitory storage devices 2225, which can comprise, without limitation, local and/or network accessible storage, and/or can include, without limitation, a hard drive, a drive array, an optical storage device, a solid-state storage device such as a random access memory ("RAM") and/or a read-only memory ("ROM"), which can be programmable, flash-updateable and/or the like. Such storage devices may be configured to implement any appropriate data storage, including, without limitation, various file systems, database structures, and/or the like.

The device 2200 might also include without limitation one or more communications subsystems 2230, which can include without limitation a network communications device (wireless and/or wired), an infrared communication device, an optical communications device, a wireless communication device and/or chipset (such as a Bluetooth® device, an RFID device (active, passive, or battery-assisted passive), an 802.11 device, a WiFi device, a WiMax device, cellular communication facilities), any kind of signaling circuitry or communications device, including any kind of EMF transmitter/receiver device (which may, without limitation, transmit, receive, both transmit and receive, reflect and/or alter an outside transmission, and the like) a wireless communications device, and/or the like. Bluetooth is a proprietary open wireless technology standard for wirelessly exchanging data, and RFID, Radio-frequency identification, is a wireless non-contact technology that uses radio-frequency electromagnetic fields to transfer data. Communications subsystem 2230 could include, without limitation, one or more antenna devices to broadcast and receive electromagnetic signals. Communications subsystem 2230 may permit data to be exchanged with an external and/or remote device (such as a mobile device) and/or network, other devices, and/or any other devices described herein. As described herein, the term "external device" and "remote device" may be used interchangeably, without limiting the scope of the disclosure. For example, the external device discussed above may be the same device as the remote device 930 discussed in FIG. 9.

In many embodiments, the device 2200 will further comprise a non-transitory working memory 2235, which can include a RAM or ROM device, as described above.

Other devices that communications subsystem 2230 may permit data to be exchanged with include without limitation other and/or similar embodiments of the invention in and/or on and/or throughout the body of the wearer, and/or in and/or on and/or the body or bodies of one or more other wearers of such devices.

The device 2200 also can comprise software elements, shown as being currently located within the working memory 2235, including an operating system 2240, device drivers, executable libraries, and/or other code, such as one or more programs or application(s) 2245, which may comprise computer programs provided by various embodiments, and/or may be designed to implement methods, and/or configure systems, provided by other embodiments, as described herein. Merely by way of example, one or more procedures described with respect to the method(s) discussed above might be implemented as code and/or instructions executable by a computer (and/or a processor within a computer); in an aspect, then, such code and/or instructions can be used to configure and/or adapt a general purpose computer (or other device) to perform one or more operations in accordance with the described methods.

A set of these instructions and/or code might be stored on a computer-readable storage medium, such as the storage device(s) 2225 described above. In some cases, the storage medium might be incorporated within a device, such as device 2200. In other embodiments, the storage medium might be separate from a device (e.g., a removable medium, such as a compact disc), and/or provided in an installation package, such that the storage medium can be used to program, configure and/or adapt a general purpose computer with the instructions/code stored thereon. These instructions might take the form of executable code, which can be executable by the device 2200 and/or might take the form of source and/or installable code, which, upon compilation and/or installation on the device 2200 (e.g., using any of a variety of generally available compilers, installation programs, compression/decompression utilities, etc.), then takes the form of executable code.

Substantial variations may be made in accordance with specific requirements. For example, customized hardware might also be used, and/or particular elements might be implemented in hardware, software (including portable software, such as applets, etc.), or both. Further, connection to other computing devices such as network input/output devices may be employed.

Some embodiments may employ a device (such as the device 2200) to perform methods in accordance with the disclosure. For example, some or all of the procedures of the described methods may be performed by the device 2200 in response to processor 2210 executing one or more sequences of one or more instructions (which might be incorporated into the operating system 2240 and/or other code, such as an application 2245) contained in the working memory 2235. Such instructions may be read into the working memory 2235 from another computer-readable medium, such as one or more of the storage device(s) 2225. Merely by way of example, execution of the sequences of instructions contained in the working memory 2235 might cause the processor(s) 2210 to perform one or more procedures of the methods described herein.

The terms "machine-readable medium" and "computer-readable medium," as used herein, may refer to any article of manufacture or medium that participates in providing data that causes a machine to operate in a specific fashion. In an embodiment implemented using the device 2200, various computer-readable media might be involved in providing instructions/code to processor(s) 2210 for execution and/or might be used to store and/or carry such instructions/code (e.g., as signals). In many implementations, a computer-readable medium is a physical and/or tangible storage medium and/or memory storage device. Such a medium may take many forms, including, but not limited to, non-volatile media, volatile media, and transmission media. Non-volatile media may include without limitation optical and/or magnetic and/or solid state drives, such as the storage device(s) 2225. Volatile media include, without limitation, dynamic memory, such as the working memory 2235. "Computer readable medium," "storage medium," and other terms used herein do not refer to transitory propagating signals. Common forms of physical and/or tangible computer-readable media include, for example, a floppy disk, a flexible disk, hard disk, magnetic tape, a solid state memory device, or any other magnetic medium, a CD-ROM, any other optical medium, punch cards, paper tape, any other physical medium with patterns of holes, a RAM, a PROM, an EPROM, a FLASH-EPROM, or any other memory chip or cartridge.

Various forms of computer-readable media may be involved in carrying one or more sequences of one or more instructions to the processor(s) 2210 for execution. Merely by way of example, the instructions may initially be carried on a magnetic disk and/or a solid state memory device and/or optical disc of a remote computer.

The communications subsystem 2230 (and/or components thereof) generally will receive the signals, and the bus 2205 then might carry the signals (and/or the data, instructions, etc. carried by the signals) to the working memory 2235, from which the processor(s) 2210 retrieves and executes the instructions. The instructions received by the working memory 2235 may optionally be stored on a non-transitory storage device 2225 either before or after execution by the processor(s) 2210.

The methods, systems, and devices discussed above are examples. Various embodiments may omit, substitute, or add various procedures or components as appropriate. For instance, in alternative configurations, the methods described may be performed in an order different from that described, and/or various stages may be added, omitted, and/or combined. Also, features described with respect to certain embodiments may be combined in various other embodiments. Different aspects and elements of the embodiments may be combined in a similar manner.

Specific details are given in the description to provide a thorough understanding of the embodiments. However, embodiments may be practiced without certain specific details. For example, well-known circuits, processes, algorithms, structures, and techniques have been mentioned without unnecessary detail in order to avoid obscuring the embodiments. This description provides example embodiments only, and is not intended to limit the scope, applicability, or configuration of various embodiments. Rather, the preceding description of the embodiments will provide those skilled in the art with an enabling description for implementing embodiments. Various changes may be made in the function and arrangement of elements without departing from the spirit and scope of various embodiments.

Also, some embodiments were described as processes which may be depicted in a flow with process arrows. Although each may describe the operations as a sequential process, many of the operations can be performed in parallel or concurrently. In addition, the order of the operations may be rearranged. A process may have additional steps not included in the figure. Furthermore, embodiments of the methods may be implemented by hardware, software, firmware, middleware, microcode, hardware description languages, or any combination thereof. When implemented in software, firmware, middleware, or microcode, the program code or code segments to perform the associated tasks may be stored in a computer-readable medium such as a storage medium. Processors may perform the associated tasks. Additionally, the above elements may merely be a component of a larger system, wherein other rules may take precedence over or otherwise modify the application of various embodiments, and any number of steps may be undertaken before, during, or after the elements of any embodiment are implemented.

It should be noted that the method as described herein may be implemented in software. The software may in general be stored in a non-transitory storage device (e.g., memory) and carried out by a processor (e.g., a general purpose processor, a digital signal processor, and the like.)

Having described several embodiments, it will therefore be clear to a person of ordinary skill that various modifications, alternative constructions, and equivalents may be used without departing from the spirit of the disclosure.

What is claimed is:

1. A method, comprising:
sending, from a first device disposed in an oral cavity of a first being comprising a housing resistant to damage from bodily fluids and pressure, a first type of information from the oral cavity and a second type of information provided by the first being as a user selected input regarding a condition of the first being;
receiving, at a server computer, the first type of information and the second type of information from the first device;
determining, at the server computer, a first pattern in the first type of information based on determining that the second type of information is the first condition of the first being;
sending, from a second device disposed in an oral cavity of a second being comprising a housing resistant to damage from bodily fluids and pressure, the first type of information from the oral cavity and the second type of information provided by the second being as the user selected input regarding a condition of the second being;
receiving, at the server computer, the first type of information and the second type of information from the second device;
determining, at the server computer, a second pattern in the first type of information based on determining that the second type of information is the second condition of the second being;
generating, at the server computer, an association between a pattern and a condition, based on determining that
the first pattern is same as the second pattern; and
the first condition of the first being is same as the second condition of the second being.

2. The method of claim 1, wherein the first information is an identifier for one of a biomarker, analyte, molecule or characteristic detected by the device from the oral cavity associated with a substance from the oral cavity.

3. The method of claim 1 wherein the device is a piercing.

4. The method of claim 1, wherein the device is a tongue piercing.

5. The method of claim 1, wherein the first information is a cortisol molecule in saliva of the first being or the second being.

6. The method of claim 1, wherein the first information is derived using a biomolecule sensor.

7. The method of claim 6, wherein the biomolecule sensor is a plasmonic interferometer.

8. The method of claim 6, wherein the biomolecule sensor is a molecular imprinted polymer sensor.

9. The method of claim 1, wherein the first information is an electrical property of a substance in the oral cavity.

10. The method of claim 1, wherein the first information is detected from one or more of a touch sensor device, a material sensor device, a pressure sensor device, a movement tracking sensor device, an orientation sensor device, an acceleration sensor device, a temperature sensor device, an air sensor device, or a light sensor device.

11. A system, comprising:
a first device disposed in an oral cavity of a first being comprising a housing resistant to damage from bodily fluids and pressure, wherein the first device is configured to detect:
a first type of information from the oral cavity, and
a second type of information provided by the first being as a user selected input regarding a condition of the first being; and
transmit the first type of information and second type of information to a server computer;
a second device disposed in an oral cavity of a second being comprising a housing resistant to damage from bodily fluids and pressure, wherein the second device is configured to detect:
the first type of information from the oral cavity, and
the second type of information provided by the second being as a user selected input regarding a condition of the second being; and
transmit the first type of information and second type of information to the server computer;
the server computer, comprising:
a communication module, configured to:
receive a first type of information and a second type of information from the first device and the second device; and
a processor coupled to the communication module and configured to
determine a first pattern in the first type of information based on determining that the second type of information is the first condition of the first being;
determine a second pattern in the first type of information based on determining that the second type of information is the second condition of the second being; and
generate an association between a pattern and a condition, based on determining that
the first pattern is same as the second pattern; and
the first condition of the first being is same as the second condition of the second being.

12. The server computer of claim 11, wherein the first information is an identifier for one of a biomarker, analyte, molecule or characteristic detected by the device from the oral cavity associated with a substance from the oral cavity.

13. The server computer of claim 11, wherein the device is a tongue piercing.

14. The server computer of claim 11, wherein the first information is derived using a biomolecule sensor.

15. The server computer of claim 14, wherein the biomolecule sensor is a plasmonic interferometer or a molecular imprinted polymer sensor.

16. The method of claim 1, wherein the condition is one or more of anger, stress, hunger, thirst, migraine, ailment, age, height, or body weight.

17. The server computer of claim 11, wherein the condition is one or more of anger, stress, hunger, thirst, migraine, ailment, age, height, or body weight.

* * * * *